US012614641B2

(12) United States Patent
Malecha et al.

(10) Patent No.: US 12,614,641 B2
(45) Date of Patent: Apr. 28, 2026

(54) MULTI-STAGE WORKFLOW PROCESSING AND ANALYSIS PLATFORM

(71) Applicant: Biocanic Inc., San Diego, CA (US)

(72) Inventors: Jeremy Malecha, San Diego, CA (US); Andrew Reed Sullivan, San Diego, CA (US)

(73) Assignee: BIOCANIC INC., San Diego, CA (US)

( * ) Notice: Subject to any disclaimer, the term of this patent is extended or adjusted under 35 U.S.C. 154(b) by 334 days.

(21) Appl. No.: 17/459,006

(22) Filed: Aug. 27, 2021

(65) Prior Publication Data

US 2023/0060235 A1 Mar. 2, 2023

(51) Int. Cl.
| | |
|---|---|
| *G16H 80/00* | (2018.01) |
| *A61B 5/00* | (2006.01) |
| *G06F 18/10* | (2023.01) |
| *G16H 10/20* | (2018.01) |
| *G16H 15/00* | (2018.01) |
| *G16H 20/00* | (2018.01) |

(52) U.S. Cl.
CPC ........... *G16H 80/00* (2018.01); *A61B 5/7275* (2013.01); *G06F 18/10* (2023.01); *G16H 10/20* (2018.01); *G16H 15/00* (2018.01); *G16H 20/00* (2018.01)

(58) Field of Classification Search
CPC ........ G16H 80/00; G16H 10/20; G16H 15/00; G16H 20/00; G16H 10/60; G16H 40/20; A61B 5/7275; A61B 5/7435; A61B 5/024; A61B 5/14532; A61B 5/4806; A61B 5/0022; G06F 18/10
USPC .......................................... 703/2–3; 705/2–3
See application file for complete search history.

(56) References Cited

U.S. PATENT DOCUMENTS

| | | | | |
|---|---|---|---|---|
| 5,786,816 A | * | 7/1998 | Macrae .................. | G16H 40/60 |
| | | | | 128/920 |
| 5,953,704 A | * | 9/1999 | McIlroy ................. | G16H 70/20 |
| | | | | 705/2 |
| 9,536,052 B2 | | 1/2017 | Amarasingham et al. | |
| 2002/0004728 A1 | * | 1/2002 | Quattrocchi ........... | G06Q 40/08 |
| | | | | 705/3 |
| 2002/0035487 A1 | * | 3/2002 | Brummel ............... | G16H 10/60 |
| | | | | 705/3 |

(Continued)

OTHER PUBLICATIONS

Winchester, Methods for a prompt and reliable laboratory diagnosis of Pompe disease: report from an international consensus meeting, 2008, Mol Genet Metab, Mar, 93(3):275-81 (Year: 2008).*

*Primary Examiner* — Kambiz Abdi
*Assistant Examiner* — Tran N Nguyen
(74) *Attorney, Agent, or Firm* — VLP Law Group, LLP; Michel Bohn; Lance Topham

(57) ABSTRACT

An example system provides a multi-stage workflow processing and analysis platform. The system may access first data associated with a patient and provide, for display on a client device, a graphical user interface that displays workflow elements and data points of the first data. In some instances, the system may receive, via the graphical user interface, an input relating a workflow element with a data point associated with the patient, which workflow element may define an action. The system may execute the workflow including the action defined by the workflow element, receive second data based on the workflow, and provide a graphical interface displaying the first data and the second data on the client device.

19 Claims, 17 Drawing Sheets

(56) References Cited

U.S. PATENT DOCUMENTS

| | | | | |
|---|---|---|---|---|
| 2003/0065535 A1* | 4/2003 | Karlov | .................... | G16H 50/20 |
| | | | | 705/2 |
| 2006/0206358 A1* | 9/2006 | Beaver | .................... | G06Q 10/10 |
| | | | | 705/2 |
| 2009/0018862 A1* | 1/2009 | Sanger | .................... | G16H 20/00 |
| | | | | 705/2 |
| 2009/0106004 A1* | 4/2009 | Edwards | ................. | G16Z 99/00 |
| | | | | 703/6 |
| 2010/0305997 A1* | 12/2010 | Ananian | ............ | G06Q 10/0633 |
| | | | | 715/843 |
| 2011/0165542 A1* | 7/2011 | Campbell | ................ | G09B 5/00 |
| | | | | 434/219 |
| 2011/0172504 A1* | 7/2011 | Wegerich | ............ | A61B 5/6898 |
| | | | | 600/301 |
| 2014/0073882 A1* | 3/2014 | Choi | ...................... | G16H 50/20 |
| | | | | 600/301 |
| 2014/0195258 A1* | 7/2014 | Burton | .................... | G06Q 10/10 |
| | | | | 705/2 |
| 2015/0019248 A1* | 1/2015 | Anand | .................... | G06F 40/40 |
| | | | | 705/2 |
| 2016/0012194 A1* | 1/2016 | Prakash | ............ | G06Q 30/0601 |
| | | | | 705/2 |
| 2016/0098539 A1* | 4/2016 | Zamanakos | ............ | G16H 10/40 |
| | | | | 705/3 |
| 2019/0005200 A1* | 1/2019 | Zimmerman | .......... | G16H 50/30 |
| 2019/0332233 A1* | 10/2019 | Nilsson | ................ | H02M 7/521 |

* cited by examiner

MULTI-STAGE WORKFLOW PROCESSING AND ANALYSIS PLATFORM

BACKGROUND

The present specification generally relates to multi-stage workflow processing and analysis technology. For instance, some implementations of the technology describe improvements to healthcare automation, automated analysis, and integrative interfaces.

An integrative medicine practitioner may embrace concepts of integrated healthcare where a variety of health and lifestyle data influence a care and treatment plan. Data points of interest often come in the form of lab reports where a panel of complex data is reported for a patient. These lab reports originate from a variety of sources, pertain to a variety of conditions or tests, and are inconsistently formatted. With the quantity and complexity of data included in such lab reports, in addition to a variety of other information pertaining to a patient's health, such as supplements, diet, exercise, meditation, sleep data, etc., the quantity of variables, combinations, and permutations quickly exceeds the ability of a human practitioner to understand, draw conclusions, and visualize. These issues are further exacerbated when viewed over multiple patients.

Furthermore, a given lab report may indicate a number of data points that are out of a healthy range and a given patient may have a number of labs with related and/or unrelated data points that can span time and changing circumstances. It is not practical nor is it possible with current technology to manage or analyze the impact of this voluminous data in a way that insights and treatment plans can be created.

Because of these issues, patients are frequently misdiagnosed or under-diagnosed, practices are poorly managed, and data is not easily visualized. The lack of intelligent automation, analysis, and display in existing methods also significantly taxes computing devices, which must address a patient's issues separately. For instance, among many computer related issues, a practitioner may often be required to open dozens of computer windows or digital documents simultaneously thereby taxing computer resources and making it extremely difficult for the practitioner to identify trends and correlations.

SUMMARY

An improved multi-stage workflow processing and analysis platform system can be configured to perform particular operations or actions by virtue of having software, firmware, hardware, or a combination of them installed on the system that in operation causes or cause the system to perform the actions. One general aspect of the system includes a method that includes: accessing first data associated with a patient; providing, for display on a client device, a first graphical user interface displaying one or more workflow elements and at least one data point of the first data; receiving, via the first graphical user interface, an input relating a first workflow element of the one or more workflow elements with the at least one data point of the patient, the first workflow element defining a first action; executing a workflow including the first action defined by the first workflow element; receiving second data based on the workflow; and providing, for display on the client device, a second graphical user interface displaying the first data and the second data.

Some implementations may include one or more of the following features: that the first action of the first workflow element includes a lab order, the lab order requesting a lab test for the patient; automatically retrieving a lab report document based on the lab order after completion of the lab test; extracting a data value from the lab report document; determining the second data associated with the patient using the data value; normalizing one or more of the data value and a data field identifier associated with the data value; analyzing the second data using the normalized data value or the normalized data field identifier; that the lab report document is a portable document format (PDF) file; and formatting the second graphical user interface based on the second data associated with the patient, the formatting adapting the second graphical user interface to display the first data and the second data.

Some implementations may additionally or alternatively include one or more of the following features: determining a trend of a patient attribute of the patient over time based on the first data and the second data; displaying a patient progress metric in the second graphical user interface using the determined trend; the first data is derived from a first PDF of a first lab report; the second data is derived from a second PDF of a second lab report; and that the first data is derived from a first subjective survey provided to the patient, and the second data is derived from a second subjective survey provided to the patient.

Some implementations may additionally or alternatively include one or more of the following features: adapting the second graphical user interface to display patient data for a plurality of patients, the patient data including the second data, the plurality of patients including the patient; that the second graphical user interface displays the first data and the second data on a single graphical page, the single graphical page including a graphical element tracking multiple variables over time, the multiple variables indicating multiple health metrics of the patient; receiving wearable sensor data via an application programming interface coupling the system with at least one wearable electronic device, the at least one wearable electronic device sensing biometric data of the patient; analyzing the first data, the second data, and the wearable sensor data to determine a current status of at least one attribute of the patient; determining a first set of data for the patient based on the first data and the second data; determining a second set of data for one or more second patients; determining a missing data point associated with the patient based on the first set of data; inferring a value of the missing data point associated with the patient based on an analysis of the first set of data against the second set of data; receiving one or more patient indications; accessing patient data stored in a database communicatively coupled with the system; analyzing the patient data to associate a set of patient data with the one or more patient indications; and identifying one or more attributes of the set of patient data, the first data associated with the patient including the set of patient data.

Other implementations of one or more of these aspects include corresponding systems, apparatus, and computer programs, configured to perform the actions of the methods, encoded on computer storage devices.

It should be understood that the language used in the present disclosure has been principally selected for readability and instructional purposes, and not to limit the scope of the subject matter disclosed herein.

BRIEF DESCRIPTION OF THE DRAWINGS

The disclosure is illustrated by way of example, and not by way of limitation in the figures of the accompanying drawings in which like reference numerals are used to refer to similar elements.

FIG. 13 illustrates an example graphical user interface for displaying lab and other health data for a user.

DESCRIPTION

Figure 1A:
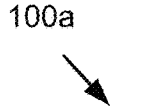
FIG. 1A is an example architecture for providing a multi-stage workflow processing and analysis platform.
Figure 1A:
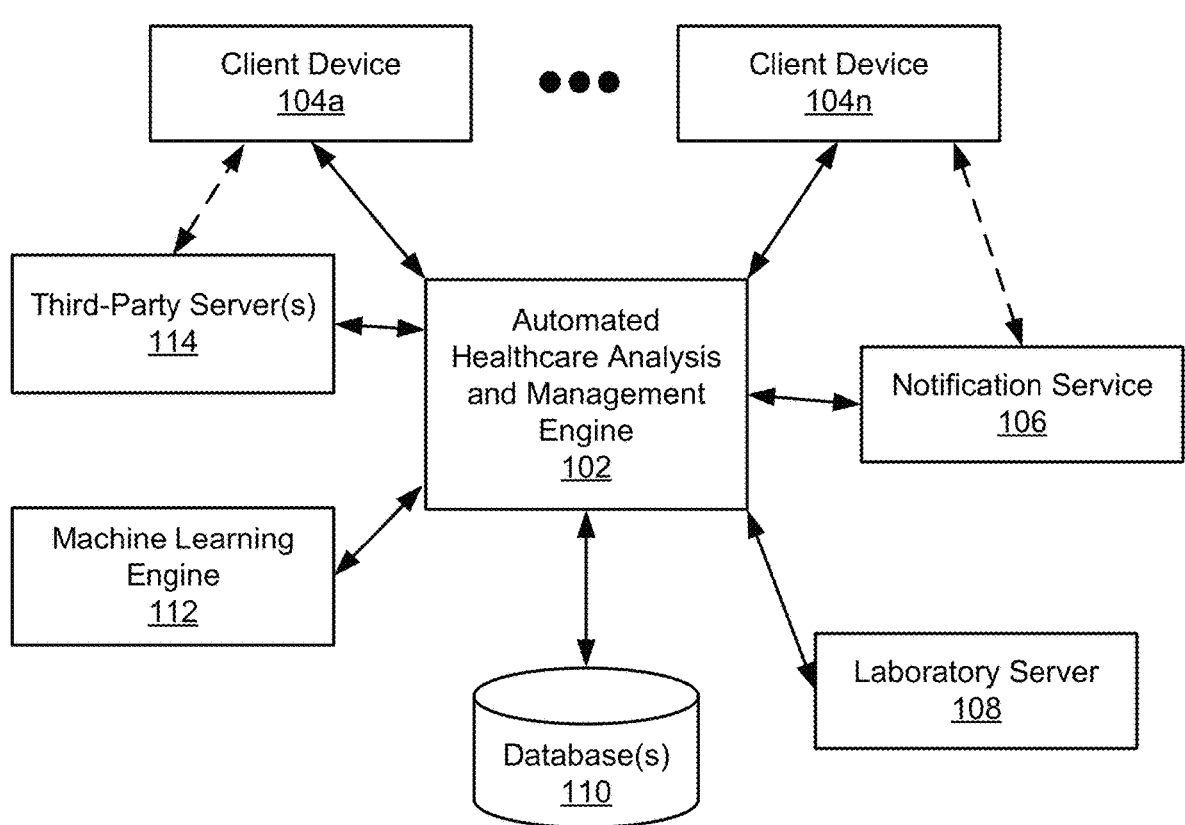

The present application generally relates to a technology platform for providing a multi-stage workflow processing and analysis. For instance, the technology describes improvements to alternative healthcare management, medical report generation, automated clinical trials and experiments, and practice management, among many other improvements. The technology described herein provides a number of improvements described throughout this specification over, for example, the previous solutions described in the Background.

Implementations of the technology described herein may include, but are not limited to, automation of lab data ingestion, presentation and/or display within a platform; the creation of workflows for automating certain workflow or protocol processes dealing with patient intake and patient treatment, progression, and tracking; and the identification of high impact data from automated analysis of large sets of patient data for use in virtual experiments.

The technology may automate intake and scheduling, lab ordering, patient follow-up, and notifications, among other things. For instance, the technology may automate steps in an intake procedure or other patient workflow or protocol, such as automatically tracking patient progress, automatically scheduling appointments after a lab result or a certain analysis or lab result, among other operations. Some implementations allow a practitioner to manually generate automated tasks and workflows, provide access to a variety of sources for aggregation, analysis, and/or automation. For instance, as described in detail below, the automation may identify data fields, extract values, make the data available for display, and/or use the data (or data derived therefrom) in the automated workflows.

For example, as part of the workflow(s), the technology may automate patient or practitioner notifications (or another component of a workflow such as in a trigger) based on configured workflows, lab data analysis, or experimental results. Other examples are possible, for instance, the technology may allow practitioners to enhance their practices, for example, by assisting practitioners in tasks ranging from patient intake, scheduling, financing, ordering, etc.

In some implementations, the technology may incorporate patient intake or other workflows that assist practitioners in scheduling and automating patient intake or other tasks that typically require a large amount of time and effort if done manually. For example, the platform described herein may provide indications or notifications to the practitioner related to patient data intake progress including follow-ups, completion status of patient intake, etc. For instance, the platform may notify a practitioner (e.g., via the practitioner's client computing device) when a patient has completed a patient intake process or sub-step, a new lab result is available for the patient, lab results are available for analysis or highlighting, among other things. In some implementations, the technology may automate steps within an intake procedure or other patient workflow or protocol, such as automatically tracking patient progress or scheduling an appointment following completion of an intake procedure, part thereof, or certain answer in the intake (or lab result or other data).

Some implementations of the technology may automatically generate and provide access to a medical report or other data. For instance, the technology may order laboratory work, detect completion of the laboratory work (e.g., through integration with another computing system or receipt of data therefrom), process and/or import a lab result(s), and/or incorporate the data to/from the workflows discussed above. For instance, the platform described herein may extract data from a lab report, automate analysis of the data (e.g., against other data for the patient or similar patients), and re-format the data and/or analysis into a dashboard view.

The technology may include interfaces adapted based on user role (e.g., lab technician, patient, practitioner, or other stakeholder), user or patient status, or attributes of the data. For instance, the system may include a graphical user interface for a centralized intake or assessment and/or a dashboard that automatically tracks and displays key health metrics, data trackers, consolidated nutritional (e.g., supplement, diet, etc.) recommendations, and ordering. For instance, the platform may display data from a range of data sources in a single view, such as multiple lab results, assessment results, intake complaints, goals, and diagnoses, which improves the viewability of this information on a limited-size display in addition to reducing the computational resources used to display such information. For instance, if a practitioner opens several lab results, assessments, and other data on a computer, significant bandwidth, random access memory, and processing resources are used. These and other implementations reduce the use of these computational resources while improving viewability on a computing device's display. The unified graphical interfaces may further speed the time used to understand a patient's health.

In some implementations, the technology may automatically analyze patient data. The platform may have access to data from a variety of sources, such as patient survey or feedback response data, scheduling data, lab data, or other health information. For example, the platform may include software configured to automate or semi-automate the retrieval or ingestion of data, for example, by automating processing of intake forms, retrieval from third-party systems, or programmatically displaying a web application part to a patient to collect data. Other data access may include automatically extracting data from lab reports (e.g., using logic configured to identify data fields and extract values), or other access.

The platform may, using the accessed data, provide automated or semi-automated functionality that assists a practitioner in making decisions and evaluating a patient by forming insights into patient issues, conditions, progress, lack of progress, difficulties, illnesses, suitable courses of treatment, etc. For example, the platform may automate or semi-automate the identification of variable or attributes that impact a patient, such as lab data that co-occurs with specific conditions, progress or lack thereof, etc., which may be automatically indicated to the practitioner (e.g., via the dashboard graphical user interface).

In some implementations, the indication(s) may be provided to an automated workflow, such as a workflow that suggests additional lab work, supplements, or treatments for the patient. For instance, the platform may provide an interface for discovering such insights, for example, via experimentation (real or simulated) using data of specific patient populations.

In some implementations, the technology may analyze data across a group of patients. For instance, the platform described herein may access and analyze data, perform data clustering, generate recommendations, etc., across a plurality of patients. For instance, the platform may aggregate data across a plurality of patients, cluster the data based on data type, tag, or value, and identify correlations, anomalies, or outliers in the data. The platform may also display data or suggestions for groups or comparable patient populations.

In some instances, the platform may generate control group(s) and simulate trials, treatments, and outcomes using the data for the plurality of patients. For instance, the platform may run data-based experimentation using data sets, models, and/or computer learning to surface relationships and test causal theories in complex, multi-variable contexts.

These and other features and advantages are described in further detail below in reference to the figures where certain functionality, features, and operations are described. It should be noted that, for each of the figures, such as the method flow-charts, operations may be reordered, removed, or changed without departing from the scope of this disclosure. For instance, operations between the methods may be exchanged or other operations may be added or changed.

The features and advantages described herein are not all-inclusive and many additional features and advantages will be apparent to a person of ordinary skill in the art in view of the figures and description. Also, it should be noted that the language used in the specification has been selected for readability and instructional purposes and not to limit the scope of the inventive subject matter.

With reference to the Figures, reference numbers may be used to refer to components found in any of the figures, regardless whether those reference numbers are shown in the Figures being described. Further, where a reference number includes a letter referring to one of multiple similar components (e.g., component 000a, 000b, and 000n), the reference number may be used without the letter to refer to one or all of the similar components.

FIG. 1A is an example architecture 100a for providing a multi-stage workflow processing and analysis platform. For ease of description herein, the architecture or the automated healthcare management system may be referred to herein simply as the platform or system. The example system 100a may include an automated healthcare analysis and management engine 102 (referred to herein as the management engine for simplicity), one or more client devices 104a . . . 104n, a notification service 106, a laboratory server 108, one or more network or device accessible databases 110, a machine learning engine 112 and/or one or more third-party server(s). Depending on the implementation, the components of the system 100a may be electronically communicatively coupled, for example, via a network or bus, for interaction with one another, although other system configurations are possible including other devices, systems, and networks. For example, the system 100a may include any number of client devices 104, third-party servers 114, or other systems and devices. In some implementations, the operations and features of various components (e.g., the automated healthcare management system) may be otherwise distributed or moved between components of the system 100a. For instance, a mobile device or web front-end application may be hosted by a third-party server 114, or another component, while a back-end application of the management engine 102 may be hosted on a first-party server or computing system.

The components of the system 100a may be coupled via a computer network or any other type of communication mechanism. For instance, a network may include, but is not limited to, one or more local area networks (LANs), wide area networks (WANs) (e.g., the Internet), virtual private networks (VPNs), wireless wide area network (WWANs), WiMAX® networks, personal area networks (PANs) (e.g., Bluetooth® communication networks), various combinations thereof, etc. These private and/or public networks may have any number of configurations and/or topologies, and data may be transmitted via the networks using a variety of different communication protocols including, for example, various Internet layer, transport layer, or application layer protocols. For example, data may be transmitted via the networks using TCP/IP, UDP, TCP, HTTP, HTTPS, DASH, RTSP, RTP, RTCP, VOIP, FTP, WS, WAP, SMS, MMS, XMS, IMAP, SMTP, POP, WebDAV, or other known protocols.

In some implementations, the servers, engines, or other components of the system 100a may have data processing, storing, and communication capabilities, as discussed elsewhere herein. For example, the component(s) may include one or more hardware servers, server arrays, storage devices and/or systems, etc. In some implementations, the component(s) may include one or more virtual servers, which operate in a host server environment.

The management engine 102 may include one or more computer programs or logic executable by a processor, for example, of a first-party server or other computing device to perform operations described herein. The management engine 102 may be communicatively coupled with other components of the system 100a receive, retrieve, transmit, or store data, for example. In some configurations, the management engine 102 may be distributed over the system 100a on disparate devices in disparate locations or may reside on the same locations.

In some implementations, the management engine 102 may include a web server that processes content requests (e.g., to or from a client device 104). The web server may include an HTTP server, a REST (representational state transfer) service, or other suitable server type. The web server may receive content requests (e.g., product search requests, HTTP requests) from client devices 104, cooperate with the management engine 102 to determine the content, retrieve and incorporate data from the data storage device 110, format the content, and provide the content to the client devices 104. In some instances, the web server may format the content using a web language and provide the content to an application or engine for processing and/or rendering to the user for display.

In some implementations, the management engine 102 may receive communications from other components of the system 100a to provide its functionality. The management engine 102 may receive information and provide information to the other components of the system 100a to generate the adaptable graphical interfaces described herein, as well as perform and provide analytics and other operations.

In some implementations, when a user navigates through an application (e.g., a mobile application, web interface, desktop program, etc.) provided by or integrated with the management engine 102, the management engine 102 may retrieve data from various components, store data on a database 110, etc.

In some implementations, as described in detail, for example, in reference to the figures, the management engine 102 may assist healthcare practitioners with implementing and enhancing their practices and provide patients with a data interface to track and manage treatments and progress. The management engine 102 has a variety of functions that assist practitioners in tasks ranging from assisting with patient intake, scheduling, financing, ordering and patient workflows to providing a digital platform for running data-based experimentation using data sets and models to surface interesting relationships and test causal theories in complex, multi-variable contexts.

The management engine 102 may operate to incorporate patient intake workflows that assist practitioners in scheduling and automating patient intake tasks that typically require a large amount of time and effort if done manually. In an example, the management engine 102 provides an automated patient intake workflow that provides a programmatic, form-based patient intake data collection. In an example, the management engine 102 provides options for a practitioner to specify the data fields or forms with data fields contained in them to be collected from a patient or set of patients along with scheduling data, including providing follow-up indications or notifications if data is not collected at an expected time.

In some implementations, the management engine 102 provides one or more channels for collection of patient data digitally. For instance, the management engine 102 may collect patient data from a client device 104 using an upload of a form, such as a portable document format (PDF) form that is filed out by a patient, a web application or application part provided to a browser of client device 104, or data gathered from other components of the system 100a, such as the notification service 106, laboratory server 108, database 110, or third-party server 114, for example.

In some implementations, the management engine 102 may provide indications or notifications to the practitioner (e.g., via the client device 104) related to patient data intake progress, including follow-ups that have been configured, completion status of patient intake, progression through a workflow or treatment protocol, a stage thereof, etc. In one example, a practitioner may be notified by the management engine 102 or notification service 106 when a patient has completed a patient intake process, treatment protocol, or sub-part.

In some implementations, the management engine 102 may automate step(s) within a workflow or protocol, such an intake procedure, by automatically triggering a next stage in the protocol or workflow, such as scheduling a patient meeting or appointment following completion of an intake procedure or part thereof, scheduling a supplement order following a lab result, etc. For instance, the management engine 102 may receive workflow data (e.g., test results) associated with a workflow element, such as a lab test element, and based on the workflow data, the management engine 102 may automatically trigger the next stage in the protocol or workflow, such as schedule an appointment, provide a notification, analyze result data in conjunction with other data to determine insights and request input, etc. As a further example, the management engine 102 may access a practitioner's calendar(s) (e.g., a Google™ Outlook™, or timeslots programmed into another accessible calendar), a patient's calendar(s), or a combination thereof, to identify an available time to schedule a meeting or appointment for the patient following a given stage. The management engine 102 may therefore provide the practitioner with the ability to automate certain tasks associated with the practice, such as using a workflow or protocol builder, as described further herein.

Figure 6:
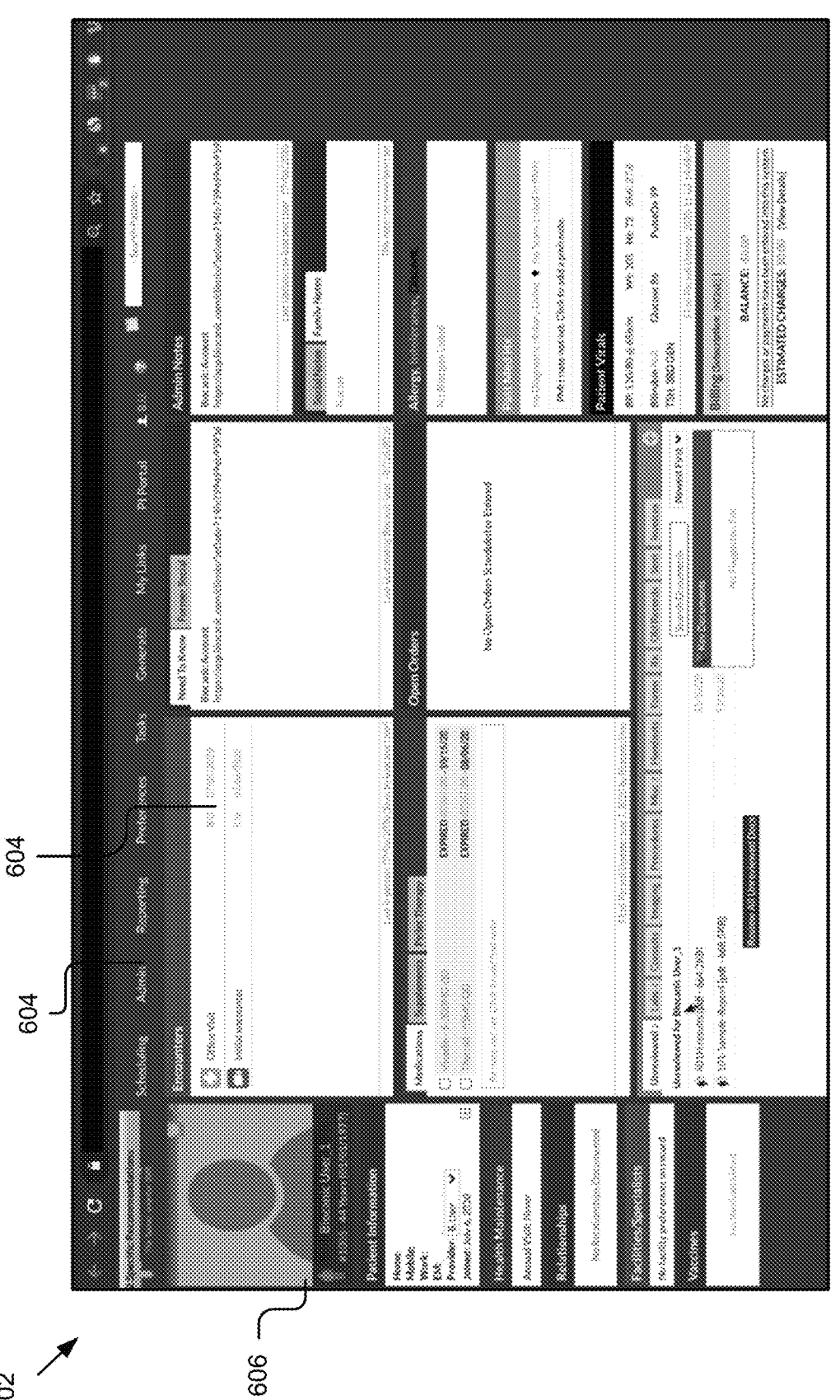
FIGS. 6 and 7 illustrate example graphical user interfaces displaying user dashboards.

The management engine 102 may provide a dashboard or other graphical user interface to the user (e.g., via client device 104). In a dashboard or graphical user interface 602 presented to the practitioner, an example of which is provided in FIG. 6, the management engine 102 may display various graphical elements for managing a practice and patients. For example, as illustrated the management engine 102 may display a dashboard 602 in a web browser interface (web application) on a client device 104 with tabs 604 for functionalities, such as scheduling, administrative settings, reporting, tasks, and a patient portal. In some implementations, the dashboard 602 may be utilized by a practitioner to configure patient intake, patient appointments, patient supplements, patient labs, patient follow-up tasks, as well as performing data analytics as further described herein. The dashboard 602 may display the data available to the management engine 102 from a variety of sources.

In some implementations, the dashboard 602 may include graphical regions 604 displaying scheduling, meetings or encounters; quick access information; notes; open lab orders; active prescriptions; health information; billing information; and various other information for a patient. An image, name, contact information, and other quick access information may be displayed at a side panel 606 for a patient. In some implementations, the dashboard may display information for multiple patients or allow the display to be quickly to another patient.

Figure 7:
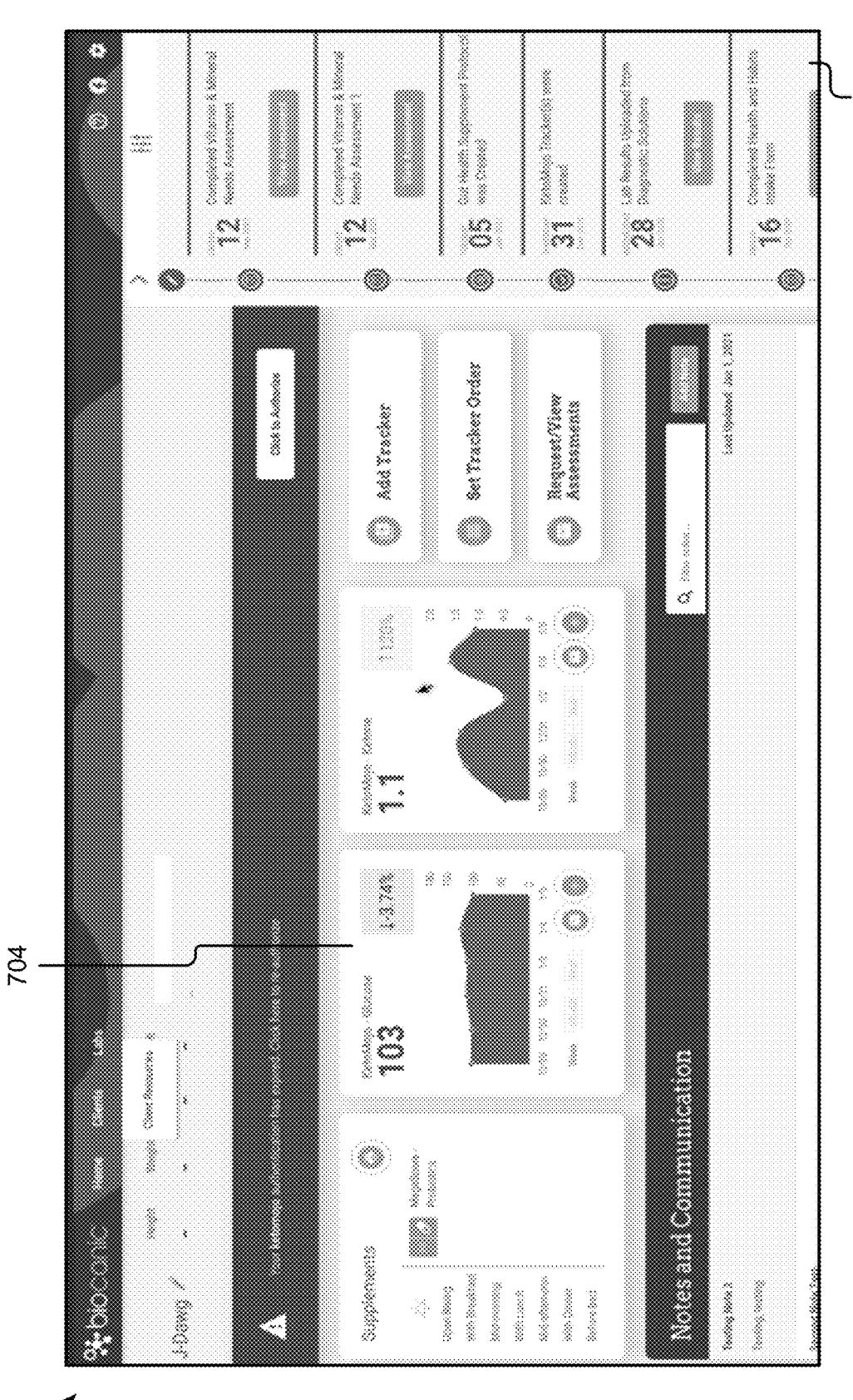

In some examples, a patient version of the dashboard 702 is provided, such as that shown in FIG. 7, which similarly presents data from the management engine 102 to a patient. As illustrated, the dashboard 702 may identify key health metrics of the patient, allow authorization for communication or data access with a biometric sensor, and provide other information. In some implementations, the patient's dashboard 702 may include various information panels graphs illustrating trends for certain health information (e.g., information over time for a biometric sensor). For instance, the dashboard 702 may include multiple panels 704 that display information from lab reports, biometric sensors, patient surveys, etc., thereby providing a compact, more easily viewable information (e.g., than viewing reports separately) as described elsewhere herein. Although not illustrated in the example of FIG. 6, the practitioner's interface(s) may also include similar informational panels to those 704 illustrated in FIG. 7.

The dashboard 702 may also include a graphical panel 706 showing a timeline of lab results, follow-ups, appointments, reminders, and other events for a patient. Depending on the implementation, the dashboard 702 may include various other elements, such as elements to add trackers (e.g., information being tracked, for example, using a biometric sensor, lab, or assessment); request, view, or fill out assessments or surveys; view supplements and recommendations; and viewing or accessing other information.

Sources of data for the management engine 102 include but are not limited to patient intake data, patient survey or feedback response data (e.g., received from a client device 104), scheduling data (e.g., derived from an external system such as a calendaring database), lab data (e.g., obtained from an external server of a lab provider, such as the laboratory server 108), and data analytics (e.g., from the output of a cloud-based machine learning provider 112). In some examples, the management engine 102 includes software configured to execute via a processor to implement certain acts or functions, such as automatic or semi-automatic processing of data, accessing and ingesting data, data analytics, etc.

In some implementations, the management engine 102 may be configured, as described herein, to partially automate data intake, such as by programmatically displaying a web application part to a patient via a client device 104 to collect data, such as patient intake or survey response data. In some instances, the management engine 102 may fully automate data access and ingestion, for example, by automatically extracting data from labs (lab reports), such as by using computer logic configured to retrieve or receive data from a lab server 108, identify one or more data fields contained in a lab report, extract value(s) associated with those data fields, and make the value(s) available for display, further processing, or communication via the management engine 102, as described below.

The management engine 102 may be communicatively coupled to access a rich set of patient data, for example, stored in one or more databases 110. Using a mechanism, such as a patient data opt-in mechanism that allows sharing data, the management engine 102 may make the set of patient data available to one or more practitioners via a graphical interface. For example, a community set of patient data, which may be anonymized and tagged for relevant attributes, may be made available to practitioners by the management engine 102. In another example, a practitioner-specific set of patient data may be made available to practitioners (e.g., only for that practitioner's patients). In another example, publicly available data may be used to enrich, supplement, or replace the set of patient data.

Accordingly, the management engine 102 may provide automated or semi-automated functionality that assists the practitioner in making decisions or forming insights into patient issues, such as difficulties, illnesses, lack of progress, suitable courses of treatment, etc. For example, the management engine 102 may automate or semi-automate the identification of variables or attributes that impact a patient, such as lab data that co-occurs with specific issues, progress or lack thereof as reported by patients, etc., which may be automatically indicated to the practitioner. The management engine 102 may communicate with external systems or devices, such as the machine learning engine 112, to assist in data processing and analysis, such as by employing machine learning, data clustering, etc., as further described elsewhere herein. In some instances, indication(s) or result data accessible by the management engine 102 may be provided as input data into an automated workflow, such as a workflow triggered based on certain patient or lab inputs that suggests additional labs, supplements or treatments for the patient. In another example implementation, the management engine 102 may provide an interface for discovering such insights, such as experimentation using data of specific patient population(s).

A client device 104 may include one or more computing devices having data processing and communication capabilities. The client device 104 may couple to and communicate with other client devices 104 and the other entities of the system 100a, for example, via a network using a wireless and/or wired connection. Examples of client devices 104 may include, but are not limited to, mobile phones, wearables, tablets, laptops, desktops, netbooks, server appliances, servers, virtual machines, TVs, etc. The system 100a may include any number of client devices 104, including client devices 104 of the same or different type. In some implementations, a client device 104 may include or couple with a biometric device, such as a smart watch, heart rate monitor, or smart body composition monitor or scale, for gathering healthcare data.

As illustrated, the management engine 102 may be communicatively coupled with a plurality of client devices 104a . . . 104n to allow communication between with multiple practitioners and patients via one or multiple devices. For instance, the management engine 102 may authenticate a user and/or client device 104 and determine that user's profile, associated role, and data access permissions using login information, web cookies, authentication tokens, etc.

In some implementations, the management engine 102 may provide documents, such as a portable document format (PDF) form that is filed out by a patient, a web application or application part provided to a browser of client device 104 that displays a graphical user interface (GUI) to a patient for data collection, for example, using a HTML, SMS, text channel, etc., or a combination of the foregoing.

A notification service or server 106 may be communicatively coupled with the management engine 102 and/or another component of the system 100a, such as a client device 104 to allow communication and/or notifications between the management engine 102 and a user. For instance, the notification service 106 may automate certain follow-up tasks, such as by sending notifications and reminders via e-mail, text message, phone calls, etc. In some implementations, a notification service 106 may be provided by a third-party, such as a customer relationship (CRM) or other messaging service (e.g., a simple notification or e-mail service provided by Amazon Web Services™). For instance, the management engine 102 may instruct the notification service 106 to communicate with a client device 104 using various contact information that may be associated with a user. In some implementations, a notification service 106 may include an e-mail or phone server, push notification service, or other device for communicating with users, for example, using client device(s) 104.

Depending on the implementation, the notification service 106 may send e-mails, text messages (e.g., short-messaging service, multimedia messaging service, chat messages, etc.), push notifications, or other messages that may include, for example, welcome information, instructions to complete a registration process, tracker reminders, assessments or surveys, task assignments, notes from a practitioner or patient, password reset notifications, contact information changes, two-factor authentication communication, and assessment or survey completion notifications.

A third-party server 114 can host services such as a third-party application (not shown), which may be individual and/or incorporated into the services provided by the management engine 102.

Although other implementations are possible, the third-party server(s) 114 may perform various operations, such as provide DNS (domain name system) services, caching of static resources (e.g., images, JavaScript libraries, etc.). In some implementations, the third-party server(s) 114 may store application configuration, such as external application programming interfaces, uniform resource locators, credentials, etc. In some implementations, the third-party server(s) 114 may store client (e.g., patient) data, such as patient details (e.g., height, weight, contact information, etc.), assessment or survey responses, parsed lab data, self-reported tracking information (e.g., daily weight measurements, activity level, resting heart rate, etc.) device or wearable tracker information (e.g., glucose measurements, etc.), although this may also be stored on the database 110 or other HIPAA compliant storage.

In some implementations, the laboratory server 108 may receive lab requests, communicate with a patient, lab technician, and/or practitioner to perform lab work, and generate lab reports. In some instances, the laboratory server 108 may be communicatively coupled with the management engine 102 to receive lab requests and/or transmit lab reports. In some implementations, the laboratory server 108 may allow lab reports to be downloaded or exported, which lab reports may then be uploaded or entered into the management engine 102.

In some implementations, the management engine 102, using the data of the laboratory server 108, may perform lab parsing, for example, when a user uploads a lab report, the management engine 102 may write the file to the database 110, convert the file (e.g., a PDF file) to text (e.g., as described below), and use that text in further processing. The management engine 102 may identify the source, subject matter, and/or format of the lab report and apply corresponding parsing logic to the lab report, so that the parsing is specifically adapted to the lab report, thereby improving the accuracy of the data import. In some instances, once the lab report has been identified, the management engine 102 may use structured key-value pairs (e.g., measurement name, measurement value) for the lab report and write the result to the database 110, for example for further display or processing, as described in further detail below.

The database 110 may include one or more information sources for storing and providing access to data, such as the data storage device 158. The database 110 may store and provide access to various data, as described in further detail elsewhere herein. For instance, the database 110 may store files for a practitioner or patient, such as resource or informational files that may be shared with a practitioner or patient, individual files, logos or images, lab report files, patient or practitioner attributes, login credentials, etc.

The machine learning engine 112 may include software or hardware that is adapted to train models, and/or analyze data using the models, for example, using various types of machine learning algorithms, as described below. In some implementations, the machine learning engine 112 may be incorporated with the management engine 102 or may be operable on a separate server and specially adapted to perform machine learning analysis of provided data.

It should be understood that the system 100*a* illustrated in FIG. 1A is representative of an example system, architecture, or platform, and that a variety of different environments and configurations are contemplated and are within the scope of the present disclosure. For instance, various acts and/or functionality may be moved from a server to a client or vice versa, data may be consolidated into a single data store or further segmented into additional data stores, and some implementations may include additional or fewer computing devices, services, and/or networks, and may implement various functionality client or server-side. Further, various entities of the system may be integrated into a single computing device or system or divided into additional computing devices or systems, etc.

Figure 1B:
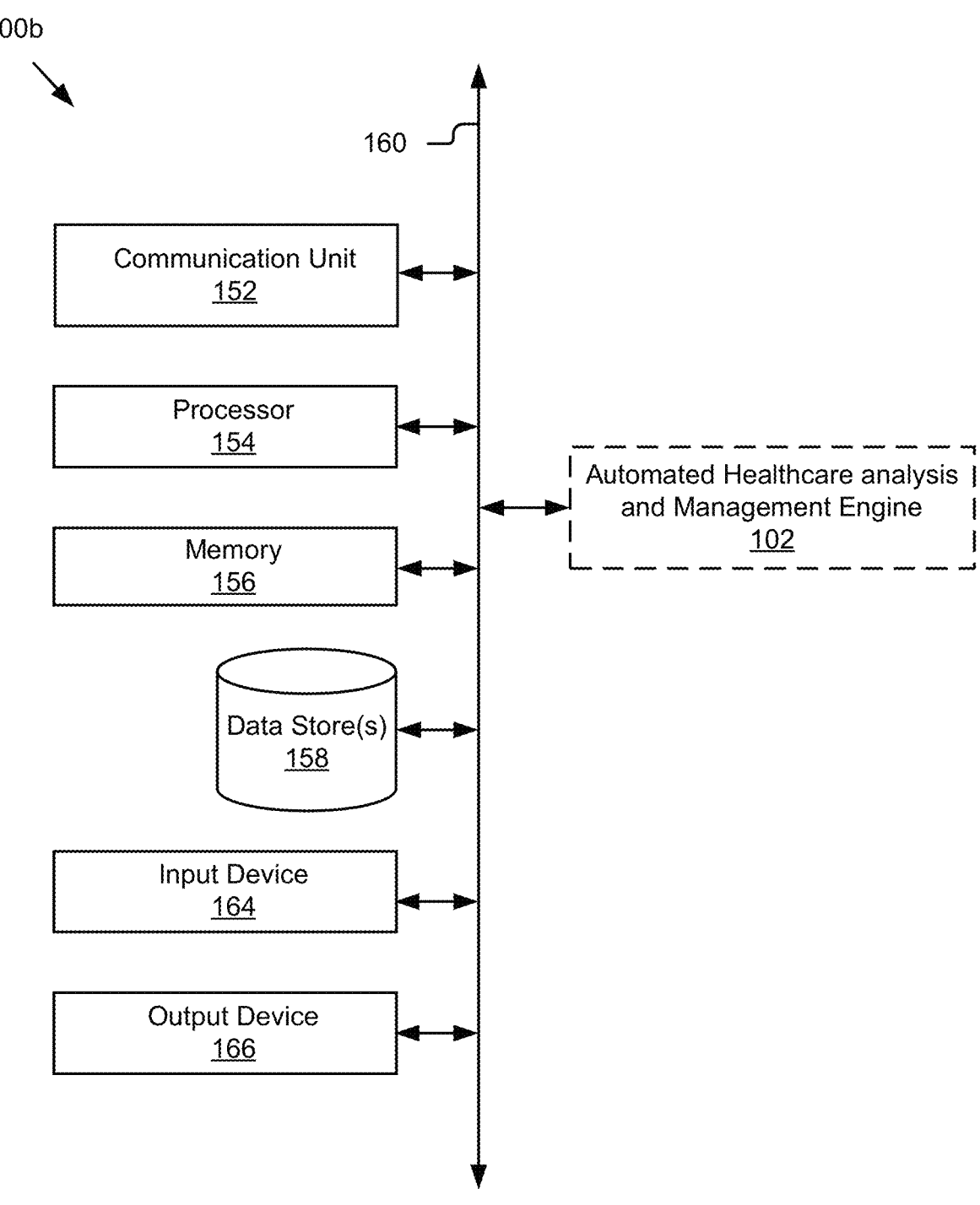
FIG. 1B illustrates an example computing device for implementing operations of a multi-stage workflow processing and analysis platform.

FIG. 1B illustrates a computing device 100*b* that can implement the operations described above, for example, the computing device may execute the management engine 102. As depicted, the computing device 100*b* may include a communication unit 152, a processor 154, a memory 156, data store(s) 158, an input device 164, an output device 166, and the management engine 102, which may be communicatively coupled by a communication bus 160. The computing device 100*b* depicted in FIG. 1B is provided by way of example and it should be understood that it may take other forms and include additional or fewer components without departing from the scope of the present disclosure. For instance, various components of the computing devices may be coupled for communication using a variety of communication protocols and/or technologies including, for instance, communication buses, software communication mechanisms, computer networks, etc. While not shown, the computing device 100*b* may include various operating systems, sensors, additional processors, and other physical configurations. Although, for purposes of clarity, FIG. 1B only shows a single communication unit 152, processor 154, memory 156, etc. It should be understood that the computing device 100*b* may include a plurality of one or more of these components.

The processor 154 may execute software instructions by performing various input, logical, and/or mathematical operations. The processor 154 may have various computing architectures to method data signals including, for example, a complex instruction set computer (CISC) architecture, a reduced instruction set computer (RISC) architecture, and/or an architecture implementing a combination of instruction sets. The processor 154 may be physical and/or virtual and may include a single core or plurality of processing units and/or cores. In some implementations, the processor 154 may be capable of generating and providing electronic display signals to a display device, supporting the display of images, capturing and transmitting images, performing complex tasks including various types of feature extraction, and sampling, etc. In some implementations, the processor 154 may be coupled to the memory 156 via the bus 160 to access data and instructions therefrom and store data therein. The bus 160 may couple the processor 154 to the other components of the computing device 100*b* including, for example, the communication unit 152, the memory 156, the input device 164, the output device 166, and the data store(s) 158.

The memory 156 may store and provide access to data to the other components of the computing device 100*b*. The memory 156 may be included in a single computing device or a plurality of computing devices. In some implementations, the memory 156 may store instructions and/or data that may be executed by the processor 154. For example, the memory 156 may store an instance of the management engine 102 and its respective components, depending on the configuration. The memory 156 is also capable of storing other instructions and data, including, for example, an operating system, hardware drivers, other software applications, data stores, etc. The memory 156 may be coupled to the bus 160 for communication with the processor 154 and the other components of the computing device 100*b*.

The memory 156 may include a non-transitory computer-usable (e.g., readable, writeable, etc.) medium, which can be any non-transitory apparatus or device that can contain, store, communicate, propagate or transport instructions, data, computer programs, software, code, routines, etc., for processing by or in connection with the processor 154. In some implementations, the memory 156 may include one or more of volatile memory and non-volatile memory (e.g., RAM, ROM, hard disk, optical disk, etc.). It should be understood that the memory 156 may be a single device or may include multiple types of devices and configurations.

The bus 160 may include a communication bus for transferring data between components of a computing device or between computing devices, a network bus system including a network (e.g., the Internet) or portions thereof, a processor mesh, a combination thereof, etc. Various components operating on the computing device 100*b* (operating systems, device drivers, etc.) may cooperate and communicate via a communication mechanism included in or implemented in association with the bus 160. The software communication mechanism can include and/or facilitate, for example, inter-method communication, local function or procedure calls, remote procedure calls, an object broker (e.g., CORBA), direct socket communication (e.g., TCP/IP sockets) among software modules, UDP broadcasts and receipts, HTTP connections, etc. Further, any or all of the communication could be secure (e.g., SSH, HTTPS, etc.).

The communication unit 152 may include one or more interface devices (I/F) for wired and wireless connectivity among the components of a system. For example, the communication unit 152 may include various types known connectivity and interface options. The communication unit 152 may be coupled to the other components of the computing device 100*b* via the bus 160. The communication unit 152 may be electronically communicatively coupled to an external network (e.g., wiredly, wirelessly, etc.). In some implementations, the communication unit 152 may link the processor 154 to the network, which may in turn be coupled to other processing systems. The communication unit 152 may provide other connections to the network and to other computing systems using various standard communication protocols.

The input device 164 may include any device for inputting information into the computing device 100*b*. In some implementations, the input device 164 may include one or more peripheral devices. For example, the input device 164 may include a sensor, a keyboard (e.g., a virtual keyboard), a pointing device (e.g., a virtual mouse device), a microphone for receiving user input via speech, an image/video capture device (e.g., camera), a touch-screen display integrated with the output device 166, etc.

The output device 166 may be any device capable of outputting information from the computing device 100*b*. The output device 166 may include one or more of a speaker, a display (LCD, OLED, etc.), a haptic device, a touch-screen display, a light indicator, etc. In some implementations, the output device 166 may be a display that can display electronic content (e.g., images, videos, etc.) with different representation effects (e.g., rewind, overlaid animation, etc.). In some implementations, the computing device 100*b* may include a graphics adapter (not shown) for rendering and outputting the electronic content for presentation on the output device 166. The graphics adapter (not shown) may be a separate processing device including a separate processor and memory (not shown) or may be integrated with the processor 154 and the memory 156.

The data store(s) 158 may be data storage device(s) for storing and providing access to data. The data stored by the data store(s) 158 may be organized and queried using any type of data stored in the data store(s) 158 (e.g., patient ID, patient attribute, health factor, lab data, etc.). The data store(s) 158 may include file systems, databases, data tables, documents, or other organized collections of data. Examples of the types of data stored in the data store(s) 158 may include user data, template data, content item data, etc.

The data store(s) 158 may be included in the computing device 100*b* or in another computing system and/or storage system distinct from but coupled to or accessible by the computing device 100*b*. The data store(s) 158 may include one or more non-transitory computer-readable mediums for storing the data. In some implementations, the data store(s) 158 may be incorporated with the memory 156 or may be distinct therefrom. In some implementations, the data store(s) 158 may store data associated with a data store management system (DBMS) operable on the computing device 100*b*. For example, the DBMS could include a structured query language (SQL) DBMS, a NoSQL DMBS, various combinations thereof, etc. In some instances, the DBMS may store data in multi-dimensional tables comprised of rows and columns, and manipulate, e.g., insert, query, update and/or delete, rows of data using programmatic operations.

The management engine 102 may include computer logic executable by the processor 154 to perform operations described herein. The management engine 102 may be coupled to the data storage device 158 to store, retrieve, and/or manipulate data stored therein and may communicatively coupled with one or more components of the device 100*b* or system 100*a* to exchange information therewith.

In some implementations, the management engine 102 may include modules or components that perform various operations. For instance, the management engine 102 may provide a platform that enables patient or practice management, lab ordering and result presentation, patient tracking and follow-up questionnaires, and automated e-clinical trials and experiments on patient data using individual modules, devices, or systems.

The components 102, 152, 154, 156, 158, 164, and/or 166, may be communicatively coupled by the bus 160 and/or the processor 154 to one another and/or to other components of a computing system. As discussed elsewhere herein, the management engine 102 may include computer logic (e.g., software logic, hardware logic, etc.) executable by the processor 154 to provide functionalities described herein.

It should be understood that the computing device 100*b* illustrated in FIG. 1B is representative of example systems and that a variety of different system environments and configurations are contemplated and are within the scope of the present disclosure. For example, various acts and/or functionality may be moved from a server to a client, or vice versa, data may be consolidated into a single data store or further segmented into additional data stores, and some implementations may include additional or fewer computing devices, services, and/or networks, and may implement various functionality client or server-side. Further, various entities of the system may be integrated into a single computing device or system or divided into additional computing devices or systems, etc.

Figure 2:
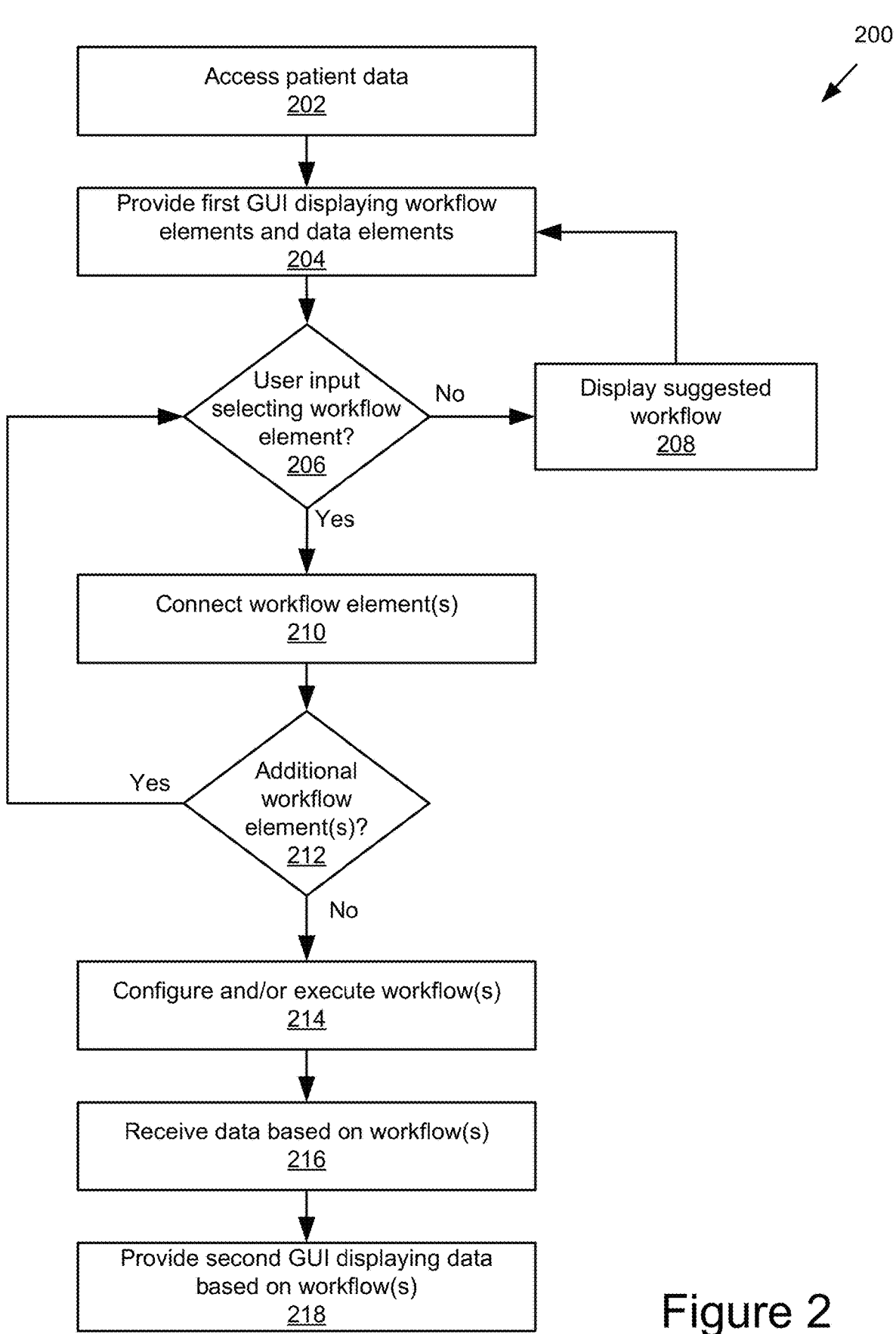
FIG. 2 illustrates an example method for managing a health care practice and to automatically generate medical reports or indications.

FIG. 2 illustrates an example method 200 for managing a health care practice, for example, to automatically generate medical reports or indications. For instance, the method may describe implementations for extracting and re-formatting data, providing automated analysis, and performing workflow analysis, for instance based on data values from lab reports, patient surveys, or other information. The method 200 may provide workflows or protocols for providing automated workflows, for instance, for medical report generation by data ingestion, extraction, filtering, and display. Accordingly, the reports and graphical interfaces described herein may allow both a patient and practitioner to easily find relevant health information quickly among a large quantity of data. The reports and interfaces may be displayed in a dedicated application or web interface, for example.

In some implementations, the management engine 102 automates data extraction and filtering to surface relevant data within dashboard views. These processes may be based on coded solutions that intake a variety of data input formats (e.g., different lab reports), automatically identify relevant data field values, and convert these values into displayable data for consumption in the dashboards/interfaces.

Further, the method 200 may integrate multiple workflows and various types of data, which provides additional improvements. For instance, the management engine 102 may receive/retrieve both objective (e.g., measured data, health tracker data, wearable data, etc.) and subjective data (e.g., periodic or daily qualitative surveys requesting subjective answers from a user where the user indicates how they feel) and then intelligently analyze and/or display the data together. For instance, the management engine 102 may determine a correlation between a sleep score (e.g., based on sleep tracking data from a smart watch or smart ring) and self-reported afternoon headache or brain fog. In some implementations, the management engine 102 may attach a flag or tag to subjective or qualitative user responses or may automatically assign a numerical value to the responses (e.g., based on predefined weights).

Figure 3:
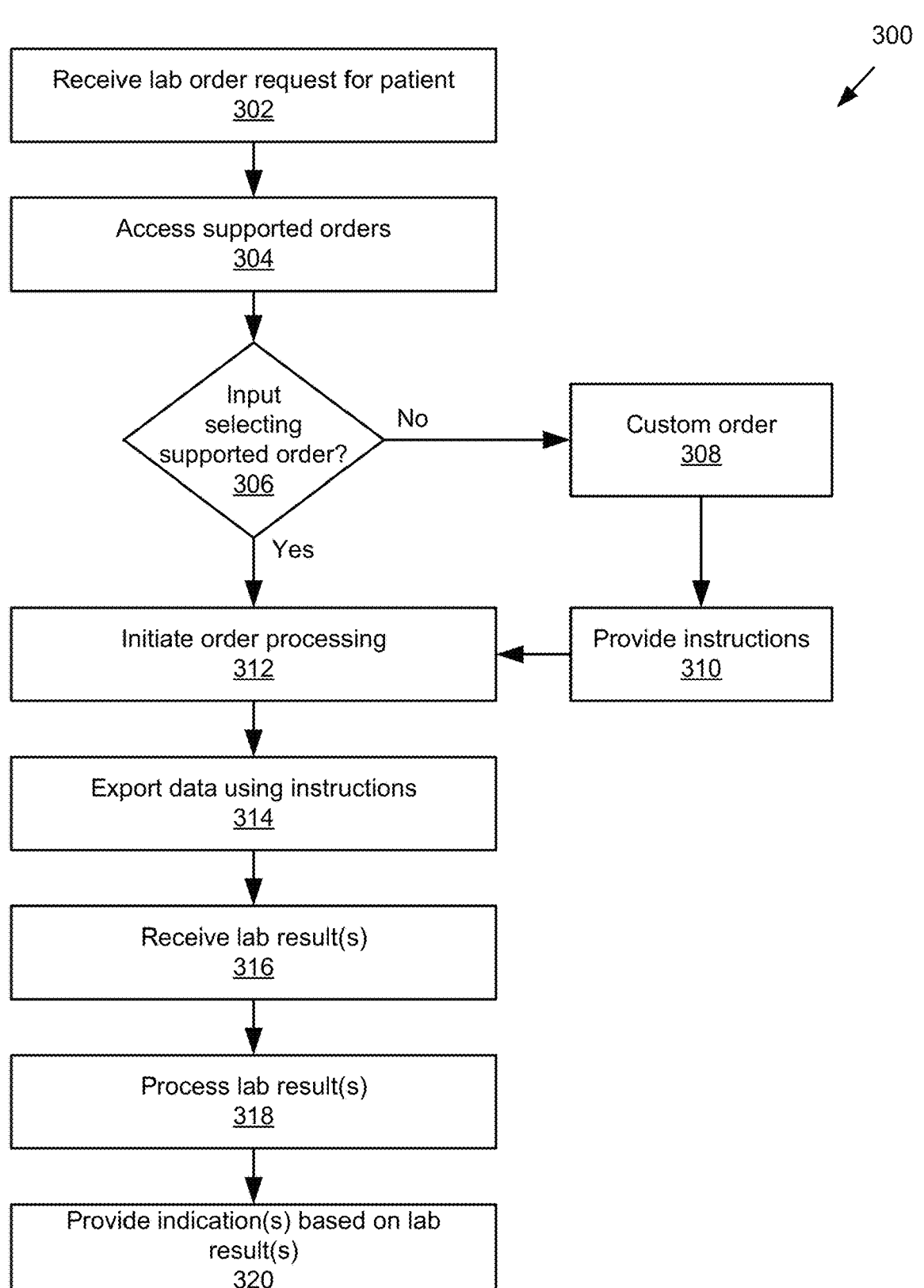
FIG. 3 illustrates an example method for automatically generating a lab order.
Figure 4:
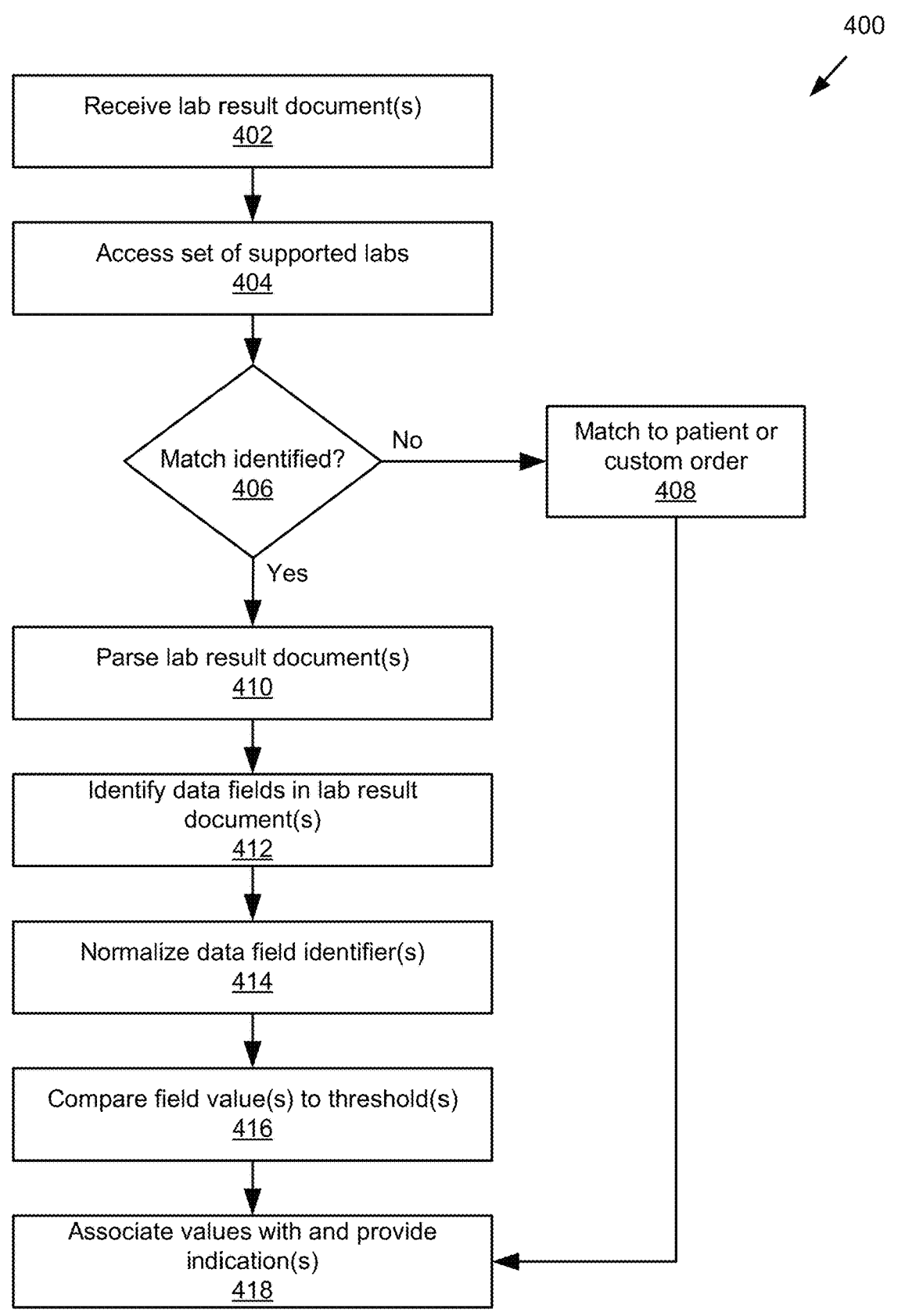
FIG. 4 illustrates an example method for automatically processing a lab document
Figure 5:
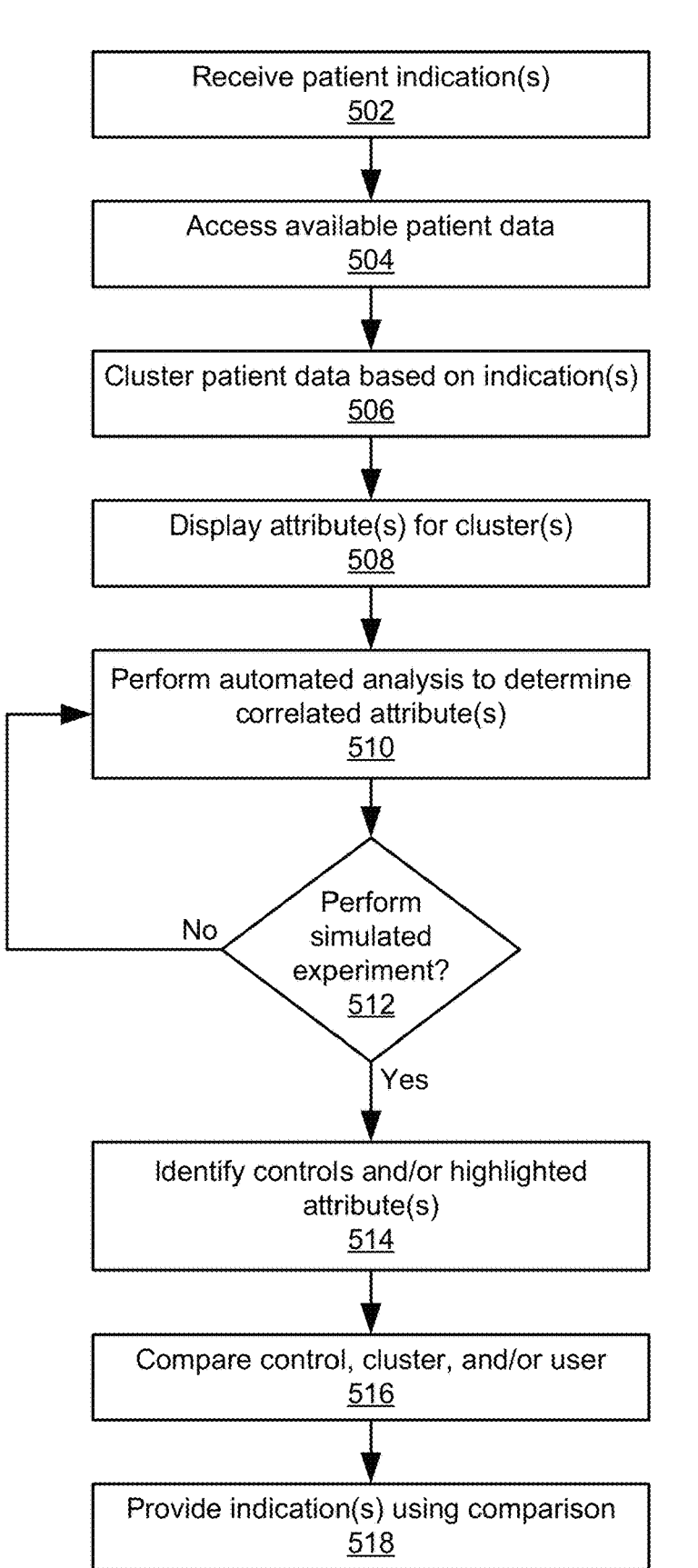
FIG. 5 illustrates an example method for automatically analyzing patient data to determine insights.

Additional or alternative details or operations of the method of FIG. 2 may be described in reference to FIGS. 3-5 herein, for example, by combining, exchanging, augmenting, removing, or reordering the operations and features, although other implementations are possible and contemplated herein.

At 202, the management engine 102 may access data associated with a patient. For example, the management engine 102 may receive intake data from a patient or another component of the system 100a. In some implementations, accessing the data may include receiving patient indications (health issues, health data, illnesses, actions, etc.), attributes, identifications, etc. For instance, the management engine 102 may access patient data stored in a database 110 communicatively coupled with the management engine 102.

For example, the management engine 102 may access the patients identification data, contact data, intake survey data, lab data, etc., in order to facilitate assisting a practitioner in building a workflow or protocol for the patient, such as an intake procedure, a recommended course of treatment, etc. The management engine 102 may access a set of user interface elements determined based on a stage or state of the patient's data, a user input, or another factor.

In some implementations, the management engine 102 may analyze the patient data to associate a set of patient data with the patient indications and, in some instances, identify attributes of the set of patient data and use the identified attributes or other parsed data to perform further actions, as described below.

At 204, the management engine 102 may provide a first graphical user interface displaying one or more workflow elements and data elements. For instance, the management engine 102 may display a user selectable element associated with at least one data point of the accessed data.

In some implementations, the management engine 102 may recommend that a certain form be sent to a patient based on the accessed data and using the contact information. Similarly, if the patient has completed an intake survey (e.g., in the accessed data), the management engine 102 may recommend an initial set of labs to be ordered for the patient (e.g., based on the intake survey data) and display the same via a graphical user interface provided to the practitioner. As another example, if the patient has completed the intake process and started on a given treatment protocol, the management engine 102 may display recommended next steps as interface elements to the practitioner.

At 206, the management engine 102 may determine whether a user input selecting the workflow element has been received. For instance, the management engine 102 may receive, via a graphical user interface, an input relating a first workflow element or action with the data point of the patient or trigger. Accordingly, the workflow may, based on patient data, automatically perform a defined action, such as ordering a lab test (e.g., via communication with the laboratory server 108). In some instances, the management engine 102 may automatically determine the type of lab order based on the data point or a parameter thereof of the patient.

For example, the management engine 102 may display a set of movable and/or connectable graphical elements to a practitioner, for example, in a graphical user interface that permits drag and drop functionality. This functionality may permit the practitioner to specify stages of a workflow or protocol, for example, to order a particular lab test, recommend supplements or other actions, and schedule a follow-up appointment with the patient (e.g., via the notification service 106).

At 208, the management engine 102 may display a suggested workflow (or workflow element), for example, if no workflow is already selected (e.g., if the user pauses). In some implementations, the management engine 102 may recommend a workflow including one or more steps, such as ordering lab tests or recommending supplements. For instance, the management engine 102 may access patient intake data, patient feedback or survey response data, lab data, results of prior experiments run by a practitioner, etc., and, based on this data, recommend an action or workflow. For example, it may recommend a certain lab test based on the patient having diabetes, irritable bowel syndrome, or a fertility problem.

Depending on the implementation, a plurality of steps, workflows, triggers, etc., may be recommended sequentially or in parallel.

At 210, the management engine 102 may connect one or more workflow elements, triggers, data points, patients, or other elements. For example, as a practitioner provides or indicates a workflow or protocol step or stage, the management engine 102 may logically connect the elements or steps to create an automated workflow.

At 212, the management engine 102 may determine whether there are additional workflow elements, actions, or workflows, for example, which may be connected together sequentially or in parallel. If the additional workflow elements are selected or may be selected, the operations from 206 may be repeated, for example. In some implementations, an output of a first workflow may serve as a trigger or input into a second workflow or stage of the workflow.

As an illustrative example, the management engine 102 may receive a second input selecting a second workflow element that defines a second action. The workflow may be automatically executed based on the second data or trigger. For example, a first action may include transmitting a request for status information (e.g., indicating a status associated with the accessed data) to a client device 104 of a patient. For instance, the second action may include transmitting a recommendation to the patent's client device including a patient survey. The workflow element or stage may also include, for example, receiving survey responses. Additional or fewer actions may be performed.

At 214, the management engine 102 may configure and/or execute one or more workflows, for example, by executing the actions defined by the workflow elements. For example, if no more workflow elements are selected (e.g., as determined at 212), the management engine 102 may configure or logically connect workflow steps, determine which internal or external systems (e.g., components in the system 100a) to use or communicate with to detect triggers and perform actions, etc. For example, if a practitioner indicates that a workflow for a given patient includes ordering a set of labs, taking a supplement on certain days of the week, and following up in two weeks, the management engine 102 may configure a workflow automation that orders the lab test (or transmits an order to a laboratory server 108, automatically provides a display to a practitioner for ordering the lab test, etc.), orders supplements, and/or schedules a follow-up meeting on the practitioner's and patient's calendars, etc.

At 216, the management engine 102 may receive data based on the workflow(s). For instance, the management engine 102 may receive data based on the workflow, such as patient survey response data, lab results, biometric sensor data, or other results of an action of the workflow.

In some instances, the management engine 102 may receive wearable sensor data via an application programming interface coupling the management engine 102 with at least one wearable electronic device with one or more biometric sensors (e.g., heart rate information, sleep tracking information, etc.). In some instances, either as part of the workflow or separately, the management engine 102 may analyze the data, compare it to other patients, determine a trend over time, or run the data through a machine learning model to detect correlations or indications, as described below. For example, the wearable sensor data may determine a current status of a patient attribute.

In some instances, the management engine 102 may determine a trend of a patient attribute over time based on the accessed data and the data received based on the workflow, although other data (e.g., from multiple workflows, workflow steps, workflow iterations, or other sources) may be used. For instance, the management engine 102 may compare one or more key metrics or data elements over time as a trend, for example, in patient progress metric in a graphical user interface.

Although other implementations are possible and contemplated herein, the data for determining the trend or other analytics may be derived from a first lab report (e.g., in PDF or other file format) and a second lab report. Alternatively or additionally, survey response data, wearable data, composite data (e.g., based on multiple patient attributes) or other patient data may be used to determine a trend or another analytic.

At 218, the management engine 102 may provide a graphical user interface displaying data based on the workflow(s). For instance, the management engine 102 may display various data, trends, and/or analytics in the graphical interface. For instance, the graphical interface may display patient intake data, trends, various accessed data, lab results, and/or other analytics and indications in a single graphical interface on the client device. In some implementations, the graphical user interface displays the first data and the second data on a single graphical page, which may include a graphical element tracking multiple variables over time, the multiple variables indicating multiple health metrics of the patient, or other data such as a recommended action.

For example, the management engine 102 may provide practitioner and/or patient facing dashboards that display automatically curated access to lab results and tracking data. In some instances, as described below, the management engine 102 may extract data from PDF lab reports or other documents and re-format the data into various visual display formats, thereby improving data accessibility and user-experience.

In some instances, the management engine 102 (e.g., using the method 200 or other operations herein) may automatically extract and highlight data of interest to a patient or practitioner from disparate lab reports while allowing the user to stay in the context of a particular dashboard or interface, thereby avoiding the need of the user to navigate the interface to an underlying report or data. The displays or dashboards may format and organize data in a quick and efficient manner and may allow a practitioner to customize the formatting or display of the data output, for example, from a laboratory's own reporting format to a practitioner preferred format. For instance, a user may select various dashboard modules for data visualization, reporting, and practice automation.

It should be noted that the operations described in reference to the method in FIG. 2 may be changed, re-ordered, or removed from the process without departing from the scope of the technology described herein, and that the operations are not inclusive of all possible operations.

In some implementations, the management engine 102 may automate various aspects of a medical practice, for example, using the workflows and components of the system 100a. These operations may substantially improve the efficiency, reliability, and speed of patient intake, follow-up, and management. The management engine 102 may integrate, using the inputs and methods described herein, mobile or web application inputs into workflow automations for patient intake, data capture, scheduling, and tracking. The management engine 102 may also facilitate laboratory and supplement ordering in the context of a patient-care interface or dashboard. In some instances, the management engine 102 may automatically retrieve a lab report, extract data from it, and format the data for display in a dashboard view (e.g., with a customized display and highlighted data of interest based on correlations and analytics). Some implementations also provide a decision support tool, for example automated insights and content recommendations, e.g., next workflow steps, based on data accessible to the management engine 102, e.g., performing a comparison of the patient's attributes with defined factors or a comparison with other patients to identify a follow up action or recommendation provided to a user.

FIG. 3 illustrates an example method 300 for automatically generating a lab order. It should be noted that the operations described in reference to the method 300 in FIG. 3 may be changed, re-ordered, or removed from the process without departing from the scope of the technology described herein, and that the operations are not inclusive of all possible operations.

Figure 8:
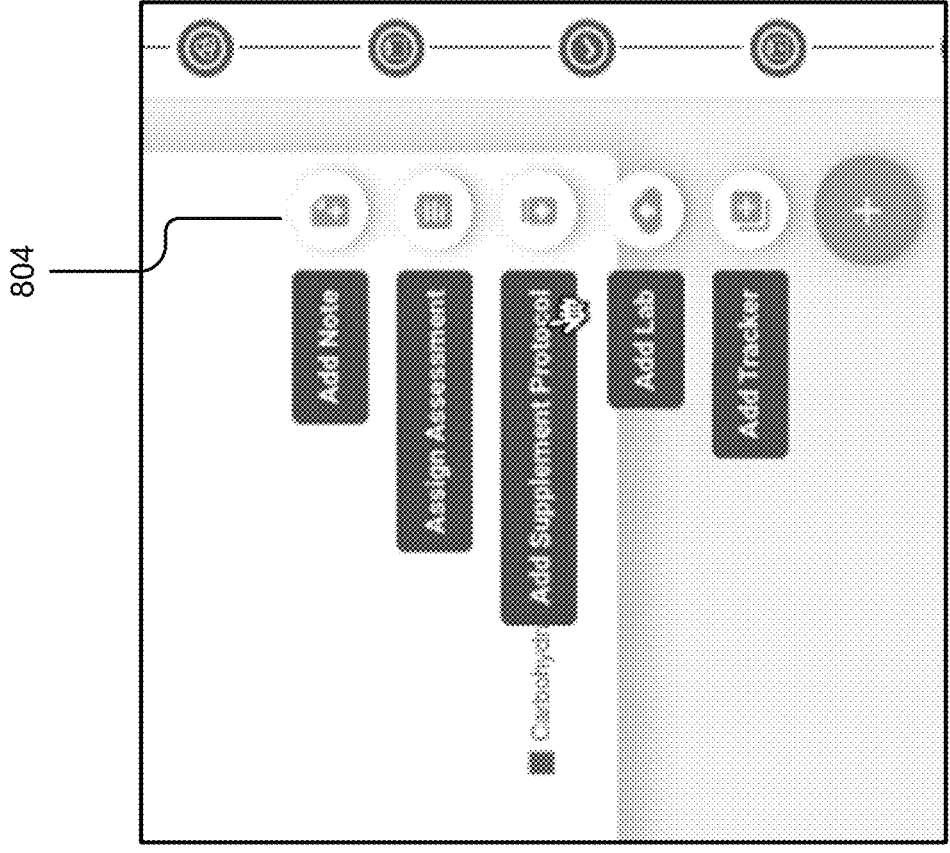
FIG. 8 illustrates an example graphical user interface for defining treatment protocols.

At 302, the management engine 102 may receive a lab order request for a patient (e.g., a request from a practitioner to schedule a tracker, order supplements, order labs, etc.), for example, as a result of initiating a workflow or protocol or via user input, such as is illustrated in FIG. 8, where an example graphical user interface 802 is provided with various graphical elements 804 for adding a note, assigning an assessment, adding a supplement protocol, adding a lab, or adding a tracker for a patient. These features permit a practitioner to configure protocols or minor workflows (e.g., single step or task) for a patient, such as a workflow or individual task to be performed by the management engine 102.

Figure 9:
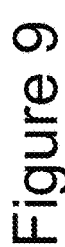
FIG. 9 illustrates an example graphical user interface for configuring health trackers.

The example of FIG. 9 illustrates an example graphical user interface 902 for configuring a new tracker. In the example of FIG. 9, a new tracker sets out various items (e.g., time for meditation) to be performed by the patient, with reminders being sent via (e.g., via a notification service 106) the platform for interfacing with the patient and tracking progress. In some instances, the tracker may track and provide automation for a certain health metric and/or treatment, for example, as part of a workflow or protocol described elsewhere herein.

Figure 10:
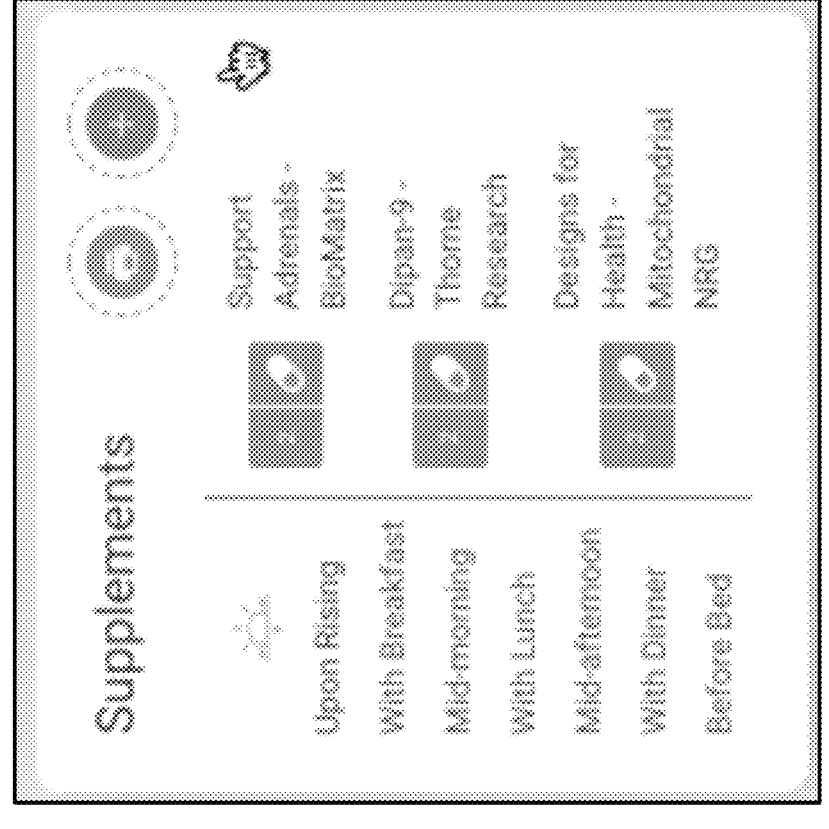
FIG. 10 illustrates an example graphical user interface for defining treatment recommendations.

FIG. 10 illustrates an example graphical user interface 1002 from a patient dashboard (e.g., from FIG. 7) that may be generated by the management engine 102 based on a supplement protocol configured by a practitioner. For instance, reminders of supplements in a supplement protocol may be provided that indicate when to take supplements, and the management engine 102 may provide an interface to the patient or practitioner to track completion thereof.

At 304, the management engine 102 may access supported orders. For example, in response to receipt of a request, the management engine 102 may access a determined set of data, such as labs from outside vendors (e.g., via the laboratory server 108). For instance, the management engine 102 may have a database of available lab tests that can be ordered as well as the details, systems, and processes for requesting each lab test.

Figure 11:
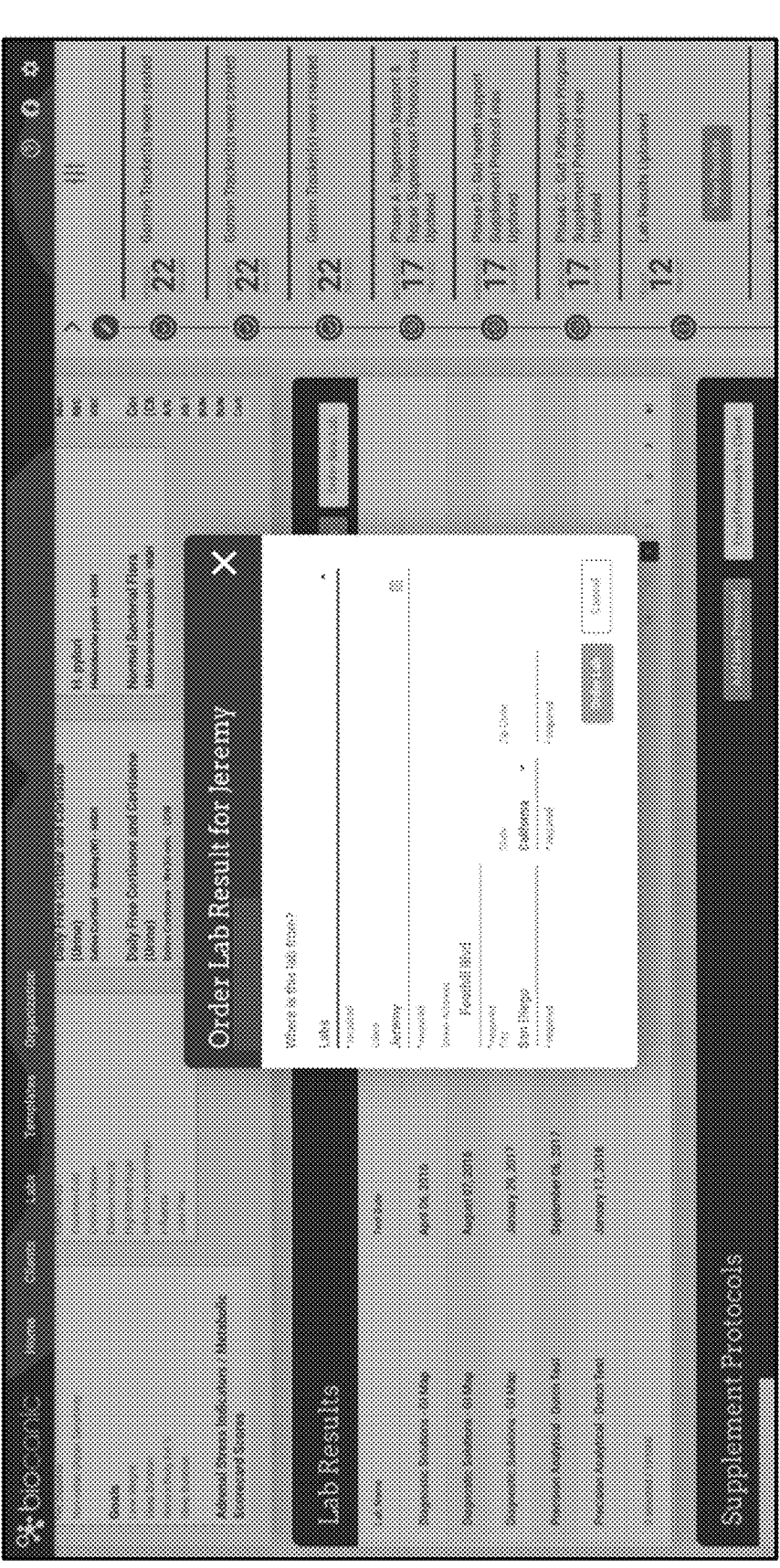
FIG. 11 illustrates an example graphical user interface for ordering a lab work for a user.

At 306, the management engine 102 may determine whether a user input selecting a supported order has been received or whether the workflow automatically selects a lab based on the patient data. For instance, if a supported lab order is selected, the method 300 may proceed to 312 using the details of the selected lab. For example, if the practitioner has configured a protocol or workflow that indicates a given lab is to be ordered (e.g., certain blood work from a certain laboratory), the management engine 102 may automate the presentation of a GUI that facilitates ordering this lab via a given vendor or may automatically communicate to order the lab test (e.g., via communication with the laboratory server 108). For example, FIG. 11 illustrates an example graphical user interface 1102 for ordering a lab via the management engine 102. For instance, when a lab ordering element is selected from a dashboard (e.g., 602 in FIG. 6), the management engine 102 may provide a form for providing information for the lab order. In some implementations, the form data for the lab order request may be automatically filled by the management engine 102 using patient and/or practitioner information.

At 308, the management engine 102 may generate a custom order. For instance, if a different lab test than those displayed is requested, the management engine 102 may provide a graphical element that receives data pertaining to the lab or that allows the practitioner to request the lab test external to the management engine 102.

At 310, the management engine 102 may provide instructions for generating a custom order. For instance, the management engine 102 may provide contact information for a laboratory, a direct link to an e-mail client or other contact method, or other means for contacting a laboratory for the custom lab test. In some implementations, the management engine 102 may allow a practitioner or admin to add a new lab test and/or provider to the list of supported lab orders by providing various information.

At 312, the management engine 102 may initiate order processing for the selected or custom order, depending on the implementation. For example, if the user indicates that a supported lab is desired, the management engine 102 may initiate the ordering process. In some implementations, data input via a graphical user interface 1102, such as illustrated in FIG. 11 or accessed automatically (e.g., from stored patient data, as part of a workflow, or a combination thereof) may be utilized by management engine 102 to contact a lab programmatically, for example, by contacting a laboratory server 108 to order the lab via API (application programming interface) call and communication routine.

At 314, the management engine 102 may export data using the provided instructions. In some implementations, an API call and/or communication routine may deliver or export lab order data from the management engine 102 to an external device, such as the laboratory server 108 or third-party server 114. In some implementations, the management engine 102 may provide a graphical user interface that is fully or partially filled out using the patient and/or practitioner data. For instance, the management engine 102 may auto-fill a lab order form from a lab provider, for example, as illustrated in FIG. 11 and described above.

Figure 12:
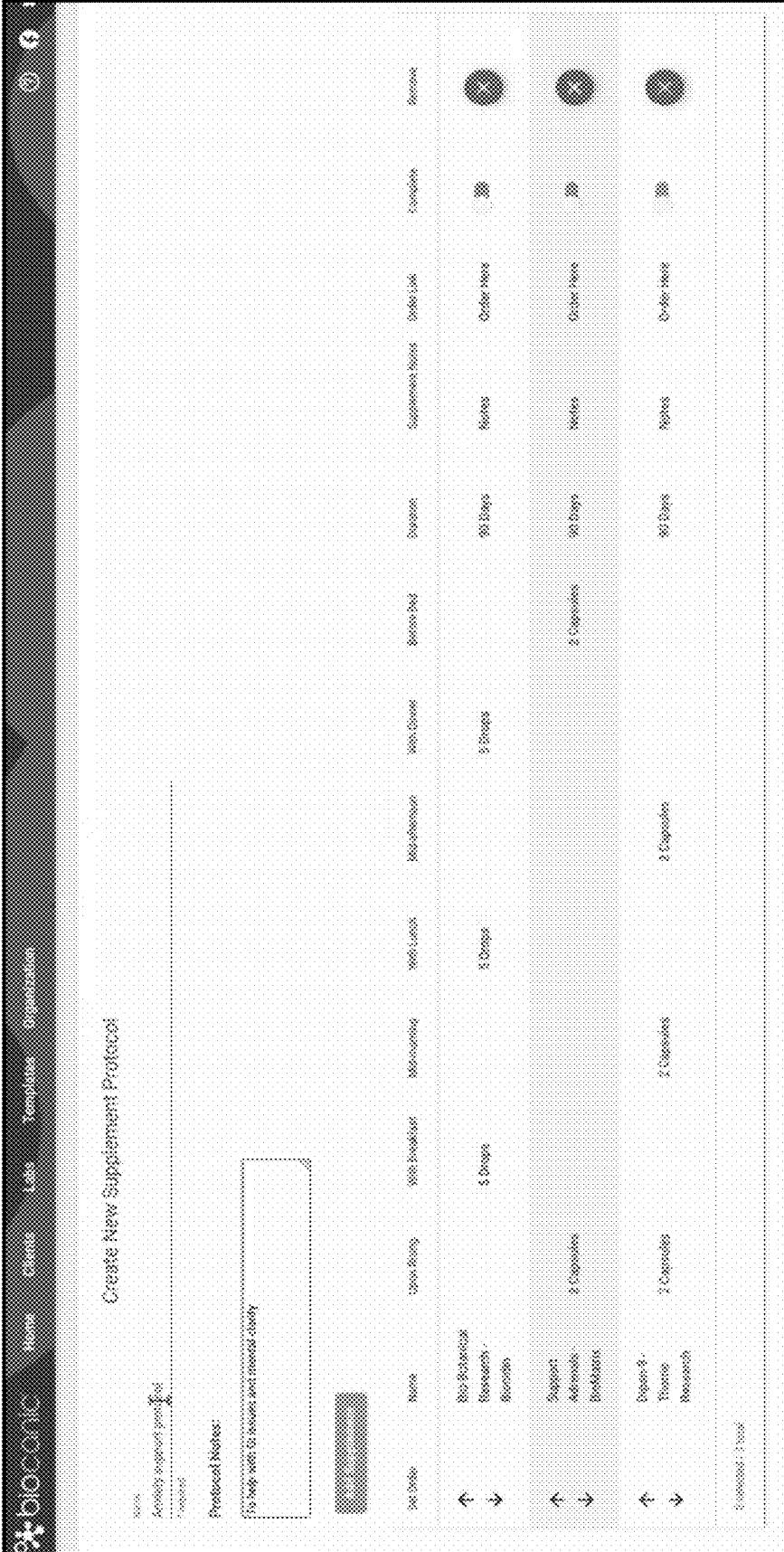
FIG. 12 illustrates an example graphical user interface for ordering supplements or other supplies for a user.

Similarly, a graphical user interface 1202 may be provided and/or filled in partially or totally via access to patient data for ordering supplements from a supplier, as illustrated in FIG. 12. For example, FIG. 12 illustrates an example graphical user interface 1202 via which a practitioner and/or patient may order supplements, set reminders, or provide other information. For instance, the interface 1202 allows a user to create a protocol or treatment plan, such as with various supplements, times, quantities, reminders, notes, links for information or ordering, and other information. For instance, a practitioner may select a supplement, indicate a quantity and timing, and other information. In some implementations, the information provided may automatically form a workflow or portion thereof and the management engine 102 may automatically send information, reminders, and/or surveys about the supplement protocol (e.g., via a notification service 106 or mobile application, etc.) to the patient or practitioner. It should be noted that the supplement protocol may be a different type of treatment protocol with other types of treatment (e.g., sleep, exercise, etc.).

At 316, the management engine 102 may receive lab result(s), for example, using the exported data, such as the lab order or result after completion of the lab test. For example, a workflow or protocol may include one or multiple steps, one of which may include automation to receive lab results for an ordered lab (e.g., via communication with the lab server 108) and/or provides order fulfillment data, such as lab results, which may be formatted in a PDF document.

At 318, the management engine 102 may process the lab result(s). In some implementations, the management engine 102 may extract a data value from a lab report document. For example, the database 110 may store formats or templates of orders that assist the management engine 102 to accurately extract data from a lab report document (e.g., by matching fields, data locations, etc.).

In some implementations, the management engine 102 may programmatically extract data from a lab report. The management engine 102 may order and process a variety of lab reports. Each report may be of a particular type and include data of a particular format, such as numeric data with defined ranges. For example, the lab report may be a document with various formats, file types, data fields, lengths, etc. The lab report may identify a laboratory, lab tests, lab results or values for each test, ranges associated with values (e.g., a normal or healthy range for a given test, such as a hormone level) and/or recommended treatments or notes.

In some implementations, the management engine may detect a lab source, format, symbol, or one or more data field and, based on the detected element, identify the document (e.g., it's fields, attributes, source, etc.) and use the identification to improve recognition accuracy. In some implementations, the management engine 102 may detect data field identifiers (e.g., certain words or symbols) that represent hormone levels, certain tests, or similar data types and use those data field identifiers to determine values of the data fields (e.g., in an adjacent field).

In some implementations, the database 110 includes a variety of templates or metadata and associated code that are used to automatically identify a particular lab report, determine the location of data of interest contained in the lab report, extract the data, and provide the data (e.g., values) for use within by the management engine 102. For example, data extracted from a lab report may be utilized by the management engine 102 for display in the dashboard, automated notification or reporting, or input into an existing workflow or protocol, etc.

Figure 13:
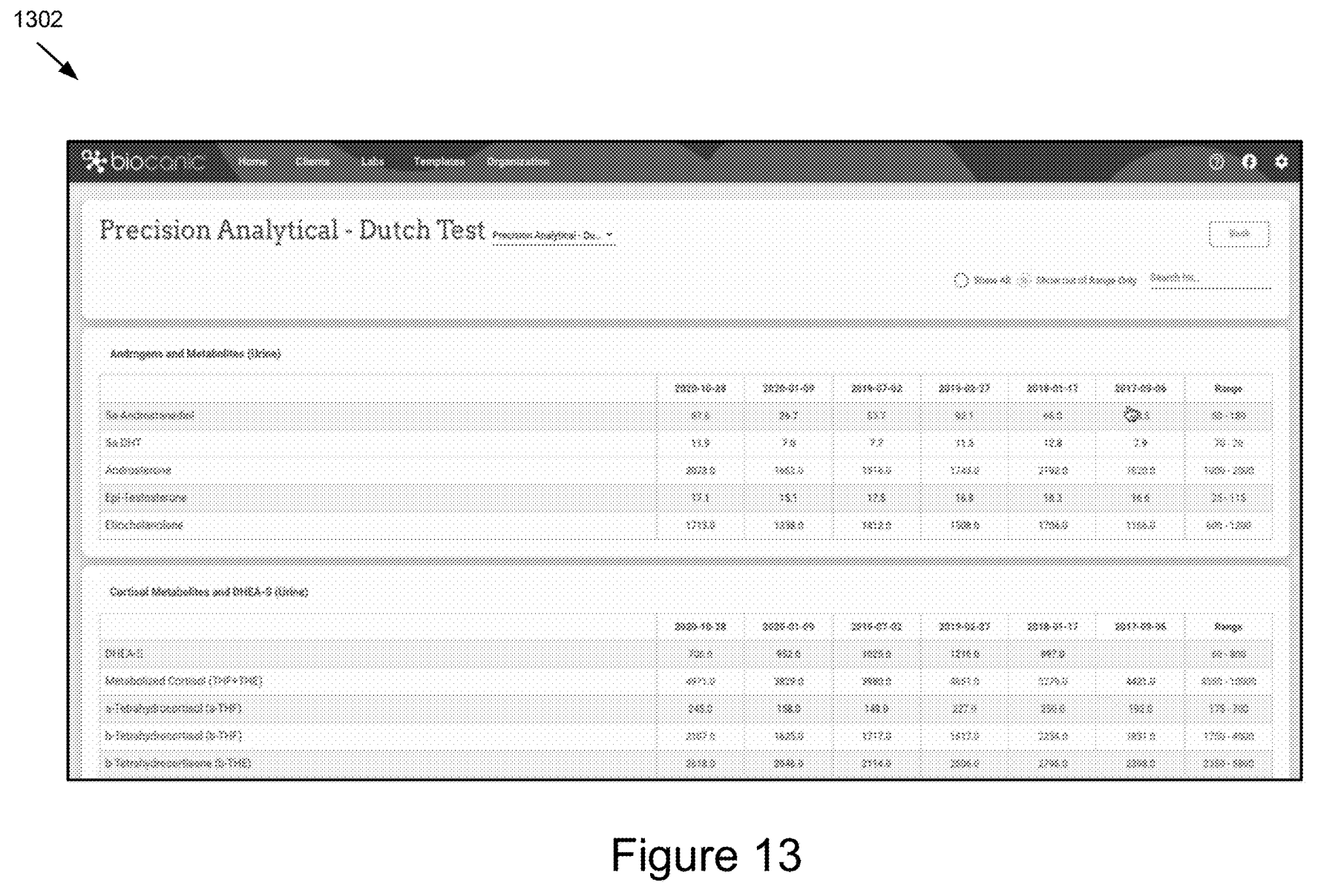

In some implementations, a lab report document may have various formats, such as a table. The management engine may use the rows and columns to extract the data fields and associated values from the document. In some implementations, whether or not the lab report included a tabular format, the management engine 102 may display lab results in a table or spreadsheet, as illustrated in the example graphical user interface 1302 illustrated in FIG. 13. As illustrated, values from individual tests (e.g., hormone levels) may be displayed over time corresponding to multiple lab result documents, thereby allowing a user to see information from several lab reports (e.g., a lab report for a Dutch Test) over time and/or over multiple patients.

Other processing is possible, such as providing lab result value(s) to an automated workflow to trigger a next stage, for example, to follow up with the patient, data analytics processing to identify similar patient populations, etc.

At 320, the management engine 102 may provide one or more indications based on the lab result(s). Accordingly, the management engine 102 may provide an indication or notification to the patient, practitioner, or both, for example, using graphical user interfaces described elsewhere herein.

FIG. 4 illustrates an example method 400 for automatically processing a lab document. For example, the management engine 102 may perform automated data extraction and filtering to surface relevant data for display or analysis.

At 402, the management engine 102 may receive or retrieve one or more data points or lab result documents, for example, based on the lab order after completion of a lab test. The lab report may include various formats of PDF documents, manual entry by a practitioner or patient, spreadsheets, direct electronic communication (e.g., with a laboratory server 108), or other means.

In some instances, a lab result document may indicate a panel of complex data that is reported for a patient. Examples of lab reports include but are not limited to gastrointestinal map (GI-MAP) labs, dried urine test for comprehensive hormones (DUTCH) labs, organic acids test (OAT), small intestine bacterial overgrowth (SIBO) tests, and IgG food sensitivity panels, among others.

At 404, the management engine 102 may access a set of supported labs, for example, there may be supported labs that have details or automation previously programmed. For instance, the database 110 may include formats or templates, data fields, markers, keywords, or other data that may be used by the management engine 102 to identify lab report documents (e.g., their source, type, etc.).

At 406, the management engine 102 may determine whether a match has been identified. For example, the management engine 102 may attempt to match a received lab report document, for example, based on data included in the lab report such as a lab name, number, data values reported in the documents, data formatting, or report formatting, etc.

At 408, the management engine 102 may match the data to a patient and/or custom order. For instance, if no match is identified at 406, the management engine 102 may match the received lab report document with a patient name or practitioner name and store it for later analysis, resolution, or manual identification.

At 410, the management engine 102 may parse the lab result document(s). For example, if the lab report received matches a known or supported lab type, the management engine 102 may parse the lab report based on the known data fields, values, or formats in the document. For example, the management engine 102 may extract a data value from the lab report document. For instance, it may utilize a lab type identification to load an extraction template and identify field(s) within the lab report, such as column and row locations.

At 412, the management engine 102 may identify data fields in the lab result document(s). For instance, the management engine 102 may use a template of the lab report type that includes data for locating the field(s) of interest in the lab report. For example, a given lab report may include data of interest in a particular alphanumeric sequence, identifiable programmatically for automated data extraction, where data of interest is identified using a known data pattern, text, position, symbol, or identifier.

At 414, the management engine 102 may normalize data field identifier(s). For example, it may normalize a data value and/or data field identifier associated with the data value. For instance, a lab result document from a first provider may have a different, but parallel, data value to a lab result document from a second provider. For instance, a first data field identifier (e.g., in a first document) may refer to an A1C level while a second data field identifier (e.g., in a second document) may refer to glycated hemoglobin. The management engine 102 may automatically match the synonymous terms with a common term that is normalized (e.g., so that both results are indicated as A1C hemoglobin). Similarly, if values or ranges are on different scales or ranges, they may be automatically normalized. Additionally, a practitioner may define preferred ranges for certain data fields, for example, to define which values are outside of normal ranges, etc., for example to modify a system provided trigger or threshold based on default values.

Normalized data field identifiers or names may be defined by a practitioner, by an administrator, by most-common usage, or by a received lab report document, although other implementations are possible and contemplated herein.

At 416, the management engine 102 may compare one or more field values to one or more thresholds. For instance, it may analyze received data (e.g., based on a workflow) using the normalized data value or normalized data field identifier.

In some implementations, the management engine 102 may automatically analyze certain lab data. For example, it may compare extracted field value(s), such as hormone levels, blood glucose, etc., in the lab(s) to thresholds, which may be provided within a lab report or stored in the database 110. For example, the management engine 102 may identify a field identifier indicating that the value in a certain field in the lab report document is a certain type of information (e.g., hormone level), determine the value in the certain fields, and then determine whether the value is within a threshold or range. The threshold or range may be provided in the lab result report, previously established in the database 110, or defined by a practitioner. In some instances, the management engine 102 may perform unit conversions to format the data per a practitioner's configurations.

Figure 14:
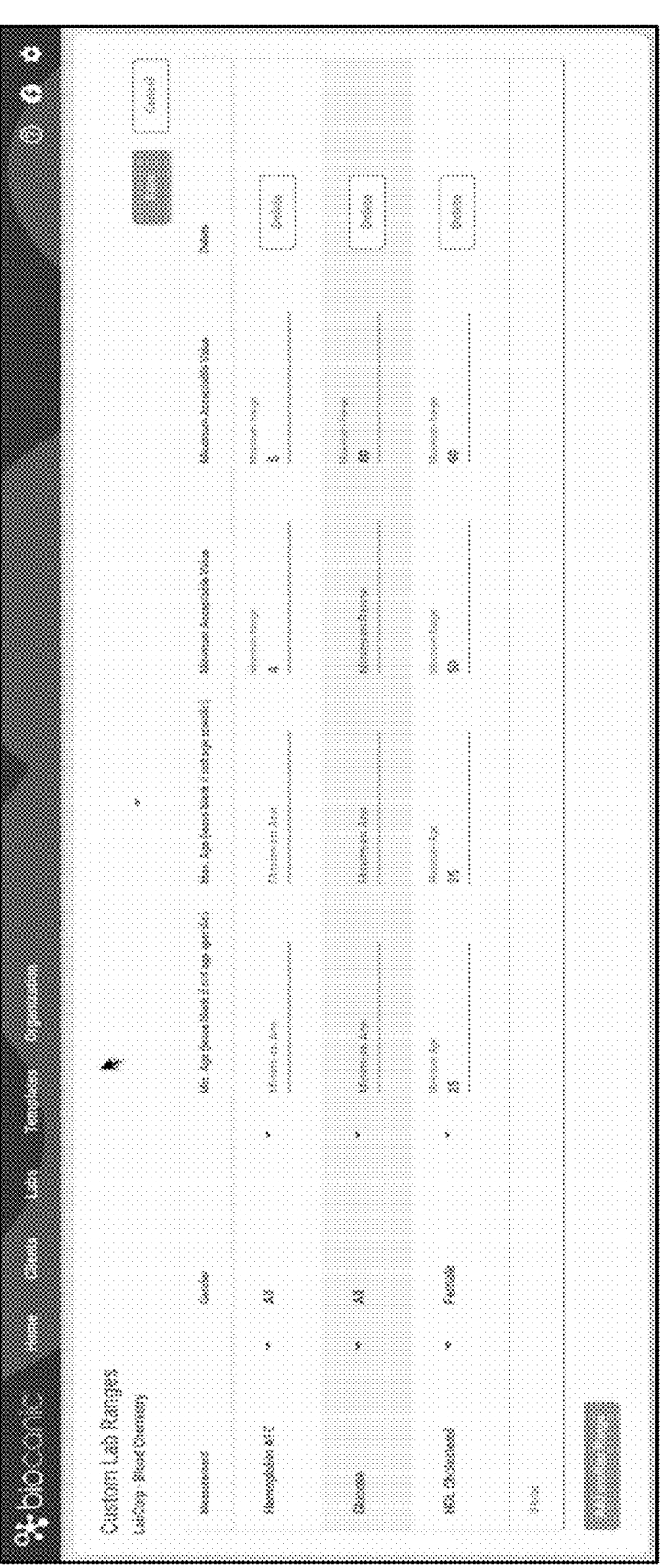
FIG. 14 illustrates an example graphical user interface for defining custom thresholds for various data values.

For example, a practitioner may indicate thresholds desired for use with a particular lab as indicated in FIG. 14, which illustrates an example graphical user interface 1402. The interface 1402 illustrates data field indicators corresponding to hormone levels in lab test results (e.g., which may be extracted from a lab report document). The interface 1402 includes graphical elements allowing a practitioner to define high and/or low values for a given data values. Based on the user-defined ranges, the management engine 102 may revise indications (e.g., diagnoses, treatments, displays, etc.) provided to a patient or practitioner. For instance, a defined value for hemoglobin A1C may adjust the graphical element displayed in test results, dashboards, etc., in various graphical user interfaces.

At 418, the management engine 102 may associate value(s) with indications and, in some instances, provide indications. For instance, if the value exceeds a normal range, the management engine 102 may determine that a patient has an issue or illness (e.g., if an A1C level is elevated, the patient may be identified as pre-diabetic). In some instances, based on defined workflows or programmed parameters, the management engine 102 may automatically recommend treatments, etc., as described elsewhere herein.

In some implementations, the management engine 102 may format a graphical user interface based on the received or determined data associated with the patient, such as the extracted data values associated with the data field identifiers. For instance, the management engine 102 may adapt the graphical user interface to display the normalized data field(s) and associated value(s) along with other patient data, analytics, or indications, as described above.

By way of example, a received lab report document may indicate that a patient's hormone levels are high, as determined by a lab supplied threshold, and the management engine 102 may map the data value to a particular indication. For example, an indication that a lab value is high, such as a color coded indication, may be automatically identified and displayed in the dashboard, whereas the original received lab report remain accessible (e.g., stored in its native format, such as PDF).

Figure 15:
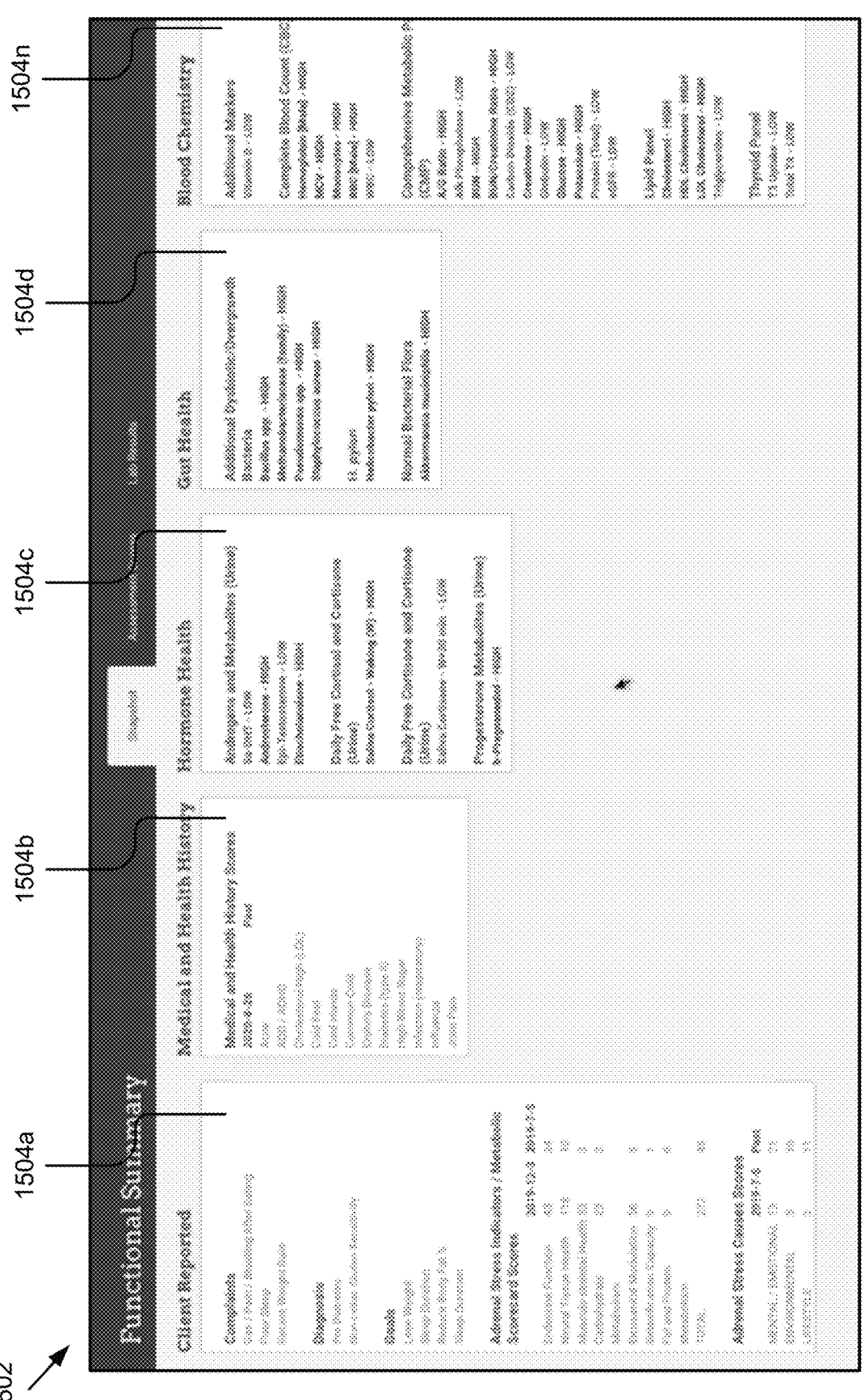
FIGS. 15 and 16 illustrate example graphical user interfaces for displaying lab results and other user information.

An example of a reporting dashboard graphical user interface 1502, including automatically extracted and analyzed lab results, is provided in FIG. 15, where certain lab results are indicated as high, low, or of normal value for a given patient. As illustrated, the management engine 102 may combine information from one or more sources, such as biometric data, patient survey data, and lab report data. In some implementations, the graphical user interface 1502 may include individual display regions 1504_a_, 1504_b_, 1504_c_, 1504_d_, and 1504_n_, which display patient data or indications divided by category. For instance, the display regions may be divided into client reported data, medical and health history, hormone health, gut health, blood chemistry, food sensitivity, and/or other categories. In some instances, where individual display regions exceed a display size, the graphical user interface 1502 may allow the regions 1504 to scroll horizontally or vertically and/or tile the regions 1504 to efficiently locate them on the display.

Figure 16:
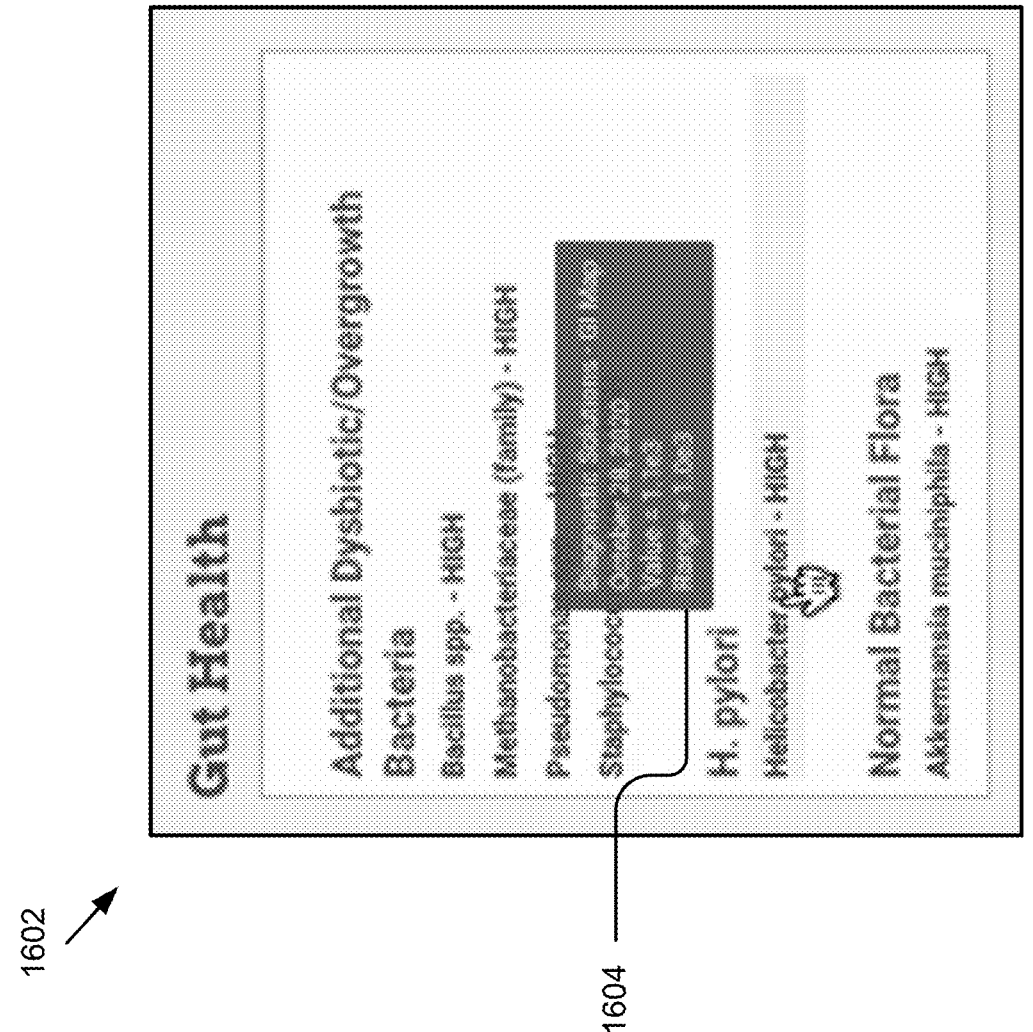

The example graphical user interface 1602 illustrated in FIG. 16 may illustrate an expansion or portion of the graphical user interface 1502. In the illustrated example, a tooltip, popup, overlay, or display window 1604 is provided with additional data or a subset of the lab report data related to the underlying display interface element. For example, data extracted and reformatted from the received lab report may be provided in the display window 1604. For instance, a user may interact with (e.g., hover over, select, etc.) a displayed data field in the dashboard (e.g., an _H. pylori_ indicator), which itself may be color coded by the management engine 102 based on analysis of the lab report and may be provided with not only the general indication mapped by the management engine 102 (e.g., "HIGH"), but may also be provided with additional data from a lab report. For example, a tool tip or window 1604 may include more specific data such as the name of the laboratory, the name of the lab report type (e.g., GI Map), a date of the lab results, values flagged as high or low in comparison to thresholds, and/or a reference range used to establish the thresholds. Accordingly, interfaces may quickly apprise the practitioner of key data in the underlying lab report without needing to navigate away from the current context of the dashboard view (e.g., a dashboard view as shown in FIG. 15), for example by accessing the original lab report document. Another example for providing lab result information is illustrated in the graphical user interface 1302 provided in FIG. 13.

FIG. 5 illustrates an example method 500 for automatically analyzing patient data, for example, to determine insights and/or perform simulated experiment using patient data.

In some implementations, in addition to providing automated analysis and data display for lab report results, the management engine 102 may be utilized to gain additional insights. For example, because practitioners struggle to interpret tests across physiological systems, they may perform a trial and error approach to test various treatments and diagnoses. For example, the gut-brain connection is well accepted in clinical physiology, but current understanding lacks a direct causal model where components of either system can be linked to each other. Due to the size and complexity of the human gut microbiome, it is nearly impossible to construct a controlled clinical trial that could establish causal linkages. More generally, the diverse data encountered and utilized by practitioners in this space has similar problems.

For instance, the management engine 102 may access, index, and use patient data across a plurality of patients to perform analysis or experimentation. The management engine 102 may allow a practitioner or patient may annotate or tag data for future use, cluster data sets based on characteristics in patient data (whether objective or subjective data, as described above), compare data sets along tagged or determined features or dimensions to highlight co-occurrences, compare data sets, track trends, and allow experimental or bioinformatics results to trigger workflow automations, such as recommendations to a patient or practitioner. Some of these comparisons or analyses may be performed using artificial intelligence, such as a trained machine learning model, a decision tree, or automated workflows, such as described below.

At 502, the management engine 102 may receive one or more patient indications. For example, the practitioner, lab result, survey, etc., may provide patient indications, interventions, or other data, as described above. In some instances, a practitioner may select a specific indication, intervention, or treatment for which to perform an analysis.

At 504, the management engine 102 may access available patient data. For example, the management engine 102 may access stored patient data (e.g., in a database 110) and use a clustering or another identification procedure to identify group(s) of patients that are similar based on attributes, for example, those who have the same indication or have had the same intervention/treatment.

At 506, the management engine 102 may cluster patient data based on the indication(s). For example, it may provide a subset of patient data by using data tags, data fields, etc., supplied by practitioners, patients, publicly available, or stored by an accessible device or database (e.g., as illustrated in FIG. 1A). For instance, a resulting subset or cluster of patient data may have similarities with respect to an indication or other data received above (e.g., at 502). In some implementations, the management engine 102 may use a clustering algorithm such as K-means, mean shift, etc.

At 508, the management engine 102 may display one or more attributes for the cluster(s). In some implementations, the management engine 102 may automatically label the group(s) or cluster(s), for example, to display attributes of each cluster.

For example, a practitioner may configure a workflow to produce a lab result for a given patient having undergone an intervention, such as taking a supplement for several weeks. Resulting lab data, when received by the management engine 102, may trigger a workflow for determining a cluster of patients with similar lab results that have also taken the supplement for the same time period. For a certain group of patients, the management engine 102 may provide (e.g., via a graphical user interface) attributes shared by the group, such as gender, age, survey responses, adherence to treatment over time, or other attributes of interest, for example, as selected by the practitioner and available from the data set. In some implementations, the management engine 102 may identify data to provide insights to other patients and their attributes and relate them back to the initial or original patient. For example, the management engine 102 may provide a score or other metric to compare attributes of the patients in the group (e.g., 80% are of a given gender, 20% are of a certain age, etc.) or a patient may have a certain similarity or distance from the mean of the group.

Here or at other points in the method 500, the management engine 102 may store data in the database 110, iterate to additional patient indications, clusters, or other data, or perform other operations. In some implementations, if a practitioner or the management engine 102 determines that a cluster or result is not useful (e.g., with insufficient p value or correlation coefficient), the management engine 102 may determine a new patient indicator and/or cluster of patients, etc., for which to perform analysis.

At 510, the management engine 102 may perform automated analysis to determine correlated attribute(s), for example, between patients, trends for a patient, treatments, etc. For instance, the management engine 102 may determine and/or highlight common or similar attributes among patients or over time for a patient. For example, if a cluster of patients have afternoon fatigue, the management engine 102 may determine that the patients also have a certain hormone outside a defined or "normal" range. It may then highlight or otherwise identify the correlated attribute (e.g., the afternoon fatigue and/or the certain hormone).

At 512, the management engine 102 may determine whether to perform a simulated experiment. For instance, a practitioner may provide a user input instructing the management engine 102 to perform a simulated experiment on patient data, for example, by considering a group of similar patients as an experimental group for a virtualized randomized clinical trial, for instance, by retroactively examining patient data and/or indicating a clinical trial that may be performed.

In some implementations, the management engine 102 or practitioner may select a different indication, treatment, or attribute (e.g., a highlighted correlated attribute) for which to perform an analysis or experiment.

At 514, the management engine 102 may identify controls and/or highlighted attributes. For instance, it may select a suitable control group of patients from available data. For example, it may identify a control including patients that are similar to the experimental group pre-intervention (e.g., treatment) but who did not receive the intervention (e.g., patients with a null value for an attribute of interest in the data set). In some implementations, the practitioner may provide user input to guide the selection, such as by providing indications of attributes that the control group should or should not have (e.g., age, gender, physical condition, etc.).

In some instances, by isolating the experimental group from the control group via difference information (in this example, the intervention), the management engine 102 may evaluate both groups to highlight attributes of each and compare the control group and the experimental cluster.

At 516, the management engine 102 may compare a control, a cluster, and/or a user, for example, by using an attribute to attribute comparison, trends across groups, machine learning, or other data analysis to determine differences, similarities, correlations, and or potential causal connections. For instance, a computer learning model may be trained based on a training data set from a plurality of patients, validated using a validation data set, and/or applied to a given (e.g., the original) patient to perform automated analysis of the patient's data (e.g., to determine indications, treatments, attributes, etc.).

In some implementations, the management engine 102 may apply machine learning across broad data sets, which has the potential to establish causal linkages using real world patient data. The management engine 102 may identify correlated variables in real world patient data and perform analysis or virtual experiments. For example, because the management engine 102 may ingest and store complex sets of data across thousands of patients, it may establish correlations and linkages across the different physiological systems. Because of the exponential increase in variation across over just a few variables and or patients, the management engine 102 may use machine learning or artificial intelligence to determine causation, aid management, and inform decision making, for instance, which is not possible in the human mind or using pen and paper.

Using the datasets available to the management engine 102, such as patient data sets and other datasets that are available, a practitioner may view the associative and causal linkages between key markers (e.g., microbiome and hormonal markers or attributes). For instance, the management engine 102 may use time series data to identify correlations between interventions, patients' responses through surveys, and/or sequential lab results. A practitioner may use the management engine 102, for instance, using multi-dimensional interventional time series data, to construct virtualized randomized controlled trials, e.g., compare or predict patient responses or lab results based on prior time series data.

In some implementations, as with the display of attributes at 504, a display of attributes of each group may be useful to a practitioner to notice differences/similarities between the groups, even if not causal. For example, a control group may share an attribute (e.g., hormone level) not identified in the experimental group. The practitioner may utilize such data to expeditiously evaluate the patient and gain insights from a large amount of data. For instance, the management engine 102 may compare a control group, experimental group, and or a certain user to highlight attributes of each and noting different attributes.

In some implementations, the management engine 102 may further compare attributes of the control, experimental, or both groups with the original patient to find matching attributes or non-overlapping attributes. For example, if the control group and the experimental group differ in hormone levels, the platform may determine that the original patient also shares this difference (either as similar to the control group or to the experimental group) and display an indication thereof. This provides the practitioner with a way to quickly obtain insights from a large amount of data that would not otherwise be possible. As such, the practitioner is able to review various attributes in an automated or semi-automated manner, permitting the practitioner to save time and effort when reviewing large data sets.

For example, the management engine 102 may determine a first set of data for a first patient and a second set of data for one or more second patients. It may then determine a missing data point associated with the patient and infer a value of the missing data point associated with the patient based on an analysis of the first patient's data against that of a second patient's data. For instance, if a first patient would typically be required to get a new lab test to determine an attribute or indication, the management engine 102 may match the first user's data to that of similar patients to infer data or determine whether a lab test should be ordered for an indication (e.g., as described above).

At 518, the management engine 102 may provide one or more indication(s) using the comparison, for example, from the operation at 516. For instance, the management engine 102 may display correlations to a practitioner using a graphical user interface, which may be adapted to display patient data for a single patient or a plurality of patients.

In some implementations, the management engine 102 may run one or a set of multiple such experiments to highlight attributes of interest for review by a practitioner. For example, an automated analysis of patient data sets may be incorporated into a workflow, for example triggered by a lab result that is above or below a threshold.

In some implementations, a feedback mechanism may be provided to the practitioner, patient, administrator, or a combination thereof in order to train the system or a machine learning model. For instance, a practitioner may review highlighted attributes and/or indicate to the system if the practitioner believes these attributes are noteworthy, helpful, etc. As such, the management engine 102 may store this information for later use, for example, in weighting which attributes to highlight, selecting additional data to display (e.g., scoring, such as 90% of practitioners use this attribute), or performing other training or analyses.

Methods are described herein; however, it should be understood that the methods are provided by way of example, and that variations and combinations of these methods, as well as other methods, are contemplated. For example, in some implementations, at least a portion of one or more of the methods represent various elements of one or more larger methods and may be concatenated or various steps of these methods may be combined to produce other methods which are encompassed by the present disclosure. Additionally, it should be understood that various operations in the methods may in some cases be iterative, and thus repeated as many times as necessary generate the results described herein. Further the ordering of the operations in the methods is provided by way of example and it should be understood that various operations may occur earlier and/or later in the method without departing from the scope thereof.

In the above description, for purposes of explanation, numerous specific details are set forth in order to provide a thorough understanding of the present disclosure. However, it should be understood that the technology described herein can be practiced without these specific details. Further, various systems, devices, and structures are shown in block diagram form in order to avoid obscuring the description. For instance, various implementations are described as having particular hardware, software, and user interfaces. However, the present disclosure applies to any type of computing device that can receive data and commands, and to any peripheral devices providing services.

In some instances, various implementations may be presented herein in terms of algorithms and symbolic representations of operations on data bits within a computer memory. An algorithm is here, and generally, conceived to be a self-consistent set of operations leading to a desired result. The operations are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout this disclosure, discussions utilizing terms such as "processing," "computing," "calculating," "determining," "displaying," or the like, refer to the action and methods of a computer system that manipulates and transforms data represented as physical (electronic) quantities within the computer system's registers and memories into other data similarly represented as physical quantities within the computer system memories or registers or other such information storage, transmission or display devices.

A data processing system suitable for storing and/or executing program code, such as the computing system and/or devices discussed herein, may include at least one processor coupled directly or indirectly to memory elements through a system bus. The memory elements can include local memory employed during actual execution of the program code, bulk storage, and cache memories that provide temporary storage of at least some program code in order to reduce the number of times code must be retrieved from bulk storage during execution. Input/output or I/O devices can be coupled to the system either directly or through intervening I/O controllers. The data processing system may include an apparatus that may be specifically constructed for the required purposes, or it may comprise a general-purpose computer selectively activated or reconfigured by a computer program stored in the computer.

The foregoing description has been presented for the purposes of illustration and description. It is not intended to be exhaustive or to limit the specification to the precise form disclosed. Many modifications and variations are possible in light of the above teaching. It is intended that the scope of the disclosure be limited not by this detailed description, but rather by the claims of this application. As will be understood by those familiar with the art, the specification may be embodied in other specific forms without departing from the spirit or essential characteristics thereof. Likewise, the particular naming and division of the modules, routines, features, attributes, methodologies, and other aspects may not be mandatory or significant, and the mechanisms that implement the specification or its features may have different names, divisions and/or formats.

Furthermore, the modules, routines, features, attributes, methodologies, and other aspects of the disclosure can be implemented as software, hardware, firmware, or any combination of the foregoing. The technology can also take the form of a computer program product accessible from a computer-usable or computer-readable medium providing program code for use by or in connection with a computer or any instruction execution system. Wherever a component, an example of which is a module or engine, of the specification is implemented as software, the component can be implemented as a standalone program, as part of a larger program, as a plurality of separate programs, as a statically or dynamically linked library, as a kernel loadable module, as firmware, as resident software, as microcode, as a device driver, and/or in every and any other way known now or in the future. Additionally, the disclosure is in no way limited to implementation in any specific programming language, or for any specific operating system or environment. Accordingly, the disclosure is intended to be illustrative, but not limiting, of the scope of the subject matter set forth in the following claims.

What is claimed is:

1. A method comprising:

accessing, by one or more processors, first data associated with a patient, the first data being at least a first healthcare-related aspect of the patient;

providing, for display on a client device and by the one or more processors, one or more graphical user interfaces displaying one or more workflow elements and at least one data point of the first data;

receiving, via the one or more graphical user interfaces and the one or more processors, an input relating a first workflow element of the one or more workflow elements with the at least one data point of the patient, the first workflow element defining a first action;

executing, by the one or more processors, a workflow including the first action defined by the first workflow element;

receiving, by the one or more processors, second data based on the workflow, the second data being at least another healthcare-related aspect of the patient that is different than the first data;

providing, for display on the client device and by the one or more processors, the one or more graphical user interfaces displaying the first data and the second data;

training, by the one or more processors, one or more weights of a machine learning model using a user input indicating a relevant attribute;

automatically performing, by the one or more processors, one or more simulated experiments based on the first data, the second data, and data for multiple other patients using the trained one or more weights of the machine learning model including:

determining, by the one or more processors, a first set of patients sharing the at least another healthcare-related aspect of the patient;

determining, by the one or more processors, a second set of patients that do not share the at least another healthcare-related aspect of the patient; and determining, by the one or more processors, one or more attributes of interest based on an automated comparison of a first set of attributes of the first set of patients with a second set of attributes of the second set of patients, the one or more attributes of interest being common among the first set of attributes and the patient and being distinct from the second set of attributes;

automatically generating, by the one or more processors, the one or more graphical user interfaces that highlight one or more of the one or more attributes of interest and an automatically generated patient treatment based at least in part on the one or more attributes of interest; and causing the patient to be treated based at least in part on the automatically generated patient treatment including exporting, by the one or more processors, order instructions to a server for one or more of a prescription and a second workflow based on the one or more attributes of interest.

2. The method of claim 1, wherein:

the first action of the first workflow element includes a lab order, the lab order requesting a first lab test for the patient.

3. The method of claim 2, further comprising:

automatically retrieving, by the one or more processors, a lab report document based on the lab order after completion of the first lab test;

extracting, by the one or more processors, a data value from the lab report document; and determining, by the one or more processors, the second data associated with the patient using the data value.

4. The method of claim 3, further comprising:

normalizing, by the one or more processors, one or more of the data value and a data field identifier associated with the data value; and analyzing, by the one or more processors, the second data using the normalized data value or the normalized data field identifier.

5. The method of claim 3, wherein:

the lab report document is a portable document format (PDF) file.

6. The method of claim 3, further comprising:

formatting, by the one or more processors, the one or more graphical user interfaces based on the second data associated with the patient, the formatting adapting the one or more graphical user interfaces to display the first data and the second data.

7. The method of claim 1, further comprising:

determining, by the one or more processors, a trend of a patient attribute of the patient over time based on the first data and the second data; and displaying, by the one or more processors, a patient progress metric in the one or more graphical user interfaces using the determined trend.

8. The method of claim 7, wherein:

the first data is derived, by the one or more processors, from a first PDF of a first lab report; and the second data is derived, by the one or more processors, from a second PDF of a second lab report.

9. The method of claim 7, wherein:

the first data is derived, by the one or more processors, from a first subjective survey provided to the patient using the one or more processors; and the second data is derived, by the one or more processors, from a second subjective survey provided to the patient using the one or more processors.

10. The method of claim 1, further comprising:

adapting, by the one or more processors, the one or more graphical user interfaces to display patient data for a plurality of patients, the patient data including the second data, the plurality of patients including the patient.

11. The method of claim 1, wherein:

the one or more graphical user interfaces display the first data and the second data on a single graphical page, the single graphical page including a graphical element tracking multiple variables over time, the multiple variables indicating multiple health metrics of the patient.

12. The method of claim 1, further comprising:

receiving, by the one or more processors, wearable sensor data via an application programming interface coupling the one or more processors with at least one wearable electronic device, the at least one wearable electronic device sensing biometric data of the patient; and analyzing, by the one or more processors, the first data, the second data, and the wearable sensor data to determine a current status of at least one attribute of the patient.

13. The method of claim 1, further comprising:

determining, by the one or more processors, a first set of data for the patient based on the first data and the second data;

determining, by the one or more processors, a second set of data for one or more second patients;

determining, by the one or more processors, a missing data point associated with the patient based on the first set of data; and inferring, by the one or more processors, a value of the missing data point associated with the patient based on an analysis of the first set of data against the second set of data.

14. The method of claim 1, wherein accessing the first data associated with the patient includes:

receiving, by the one or more processors, one or more patient indications;

accessing, by the one or more processors, patient data stored in a database communicatively coupled with the one or more processors;

analyzing, by the one or more processors, the patient data to associate a set of patient data with the one or more patient indications; and identifying, by the one or more processors, one or more attributes of the set of patient data, the first data associated with the patient including the set of patient data.

15. A system comprising:

one or more processors; and a non-transitory memory storing instructions that, when executed by the one or more processors, cause the system to:

access first data associated with a patient, the first data being related to at least a healthcare-related aspect of the patient;

provide, for display on a client device, one or more graphical user interfaces displaying one or more workflow elements and the first data;

receive, via the one or more graphical user interfaces, an input relating a first workflow element of the one or more workflow elements with the first data, the first workflow element defining a first action;

execute a workflow including the first action defined by the first workflow element;

receive second data based on the workflow, the second data being at least another healthcare-related aspect of the patient that is different than the first data;

provide, for display on the client device, the one or more graphical user interfaces displaying the first data and the second data;

automatically performing one or more simulated experiments based on the first data, the second data, and data for multiple other patients including:

determining, by the one or more processors, a first set of patients sharing the at least another healthcare-related aspect of the patient;

determining, by the one or more processors, a second set of patients that do not share the at least another healthcare-related aspect of the patient; and determining, by the one or more processors, one or more attributes of interest based on an automated comparison of a first set of attributes of the first set of patients with a second set of attributes of the second set of patients, the one or more attributes of interest being common among the first set of attributes and the patient and being distinct from the second set of attributes;

automatically generate the one or more graphical user interfaces that highlight one or more of the one or more attributes of interest and one or more attributes of an automatically generated patient treatment based at least in part on the one or more attributes of interest; and cause the patient to be treated based at least in part on the automatically generated patient treatment including exporting, by the one or more processors, order instructions to a server for one or more of a prescription and a second workflow based on the one or more attributes of interest.

16. The system of claim 15, wherein:

the first action of the first workflow element includes a lab order, the lab order requesting a first lab test for the patient.

17. The system of claim 16, wherein the instructions, when executed by the one or more processors, further cause the system to:

automatically retrieve, by the one or more processors, a lab report document based on the lab order after completion of the first lab test;

extract, by the one or more processors, a data value from the lab report document; and determine, by the one or more processors, the second data associated with the patient using the data value.

18. The system of claim 17, wherein the instructions, when executed by the one or more processors, further cause the system to:

normalize, by the one or more processors, one or more of the data value and a data field identifier associated with the data value; and analyze, by the one or more processors, the second data using the normalized data value or the normalized data field identifier.

19. The system of claim 17, wherein the instructions, when executed by the one or more processors, further cause the system to:

receive workflow data associated with the first workflow element; and automatically trigger a next stage in the workflow based on the workflow data.

* * * * *